(12) United States Patent
Ozawa et al.

(10) Patent No.: US 11,505,090 B2
(45) Date of Patent: Nov. 22, 2022

(54) ARRANGEMENT STRUCTURE FOR BIOLOGICAL SENSORS

(71) Applicant: TS TECH CO., LTD., Asaka (JP)

(72) Inventors: Hidetoshi Ozawa, Shioya-gun (JP); Takayoshi Ito, Shioya-gun (JP); Kazuyuki Takasawa, Shioya-gun (JP); Yuta Iha, Shioya-gun (JP)

(73) Assignee: TS TECH CO., LTD., Asaka (JP)

( * ) Notice: Subject to any disclaimer, the term of this patent is extended or adjusted under 35 U.S.C. 154(b) by 490 days.

(21) Appl. No.: 16/500,526

(22) PCT Filed: Apr. 3, 2018

(86) PCT No.: PCT/JP2018/014243
§ 371 (c)(1),
(2) Date: Oct. 3, 2019

(87) PCT Pub. No.: WO2018/186387
PCT Pub. Date: Oct. 11, 2018

(65) Prior Publication Data
US 2020/0039382 A1 Feb. 6, 2020

(30) Foreign Application Priority Data

Apr. 3, 2017 (JP) .............................. JP2017-073719
Aug. 15, 2017 (JP) .............................. JP2017-156696
Apr. 2, 2018 (JP) .............................. JP2018-070548

(51) Int. Cl.
*B60N 2/00* (2006.01)
*A61B 5/021* (2006.01)
(Continued)

(52) U.S. Cl.
CPC ............ *B60N 2/002* (2013.01); *A61B 5/0261* (2013.01); *A61B 5/02141* (2013.01);
(Continued)

(58) Field of Classification Search
CPC . B60N 2/002; A61B 5/02141; A61B 5/02444; A61B 5/0261; A61B 5/1455; A61B 5/6893; A61B 5/721
See application file for complete search history.

(56) References Cited

U.S. PATENT DOCUMENTS

| 4,513,748 A | 4/1985 | Nowogrodzki et al. |
| 2009/0261639 A1 | 10/2009 | Hirata |

(Continued)

FOREIGN PATENT DOCUMENTS

| CN | 106073728 A | 11/2016 |
| JP | H11-34710 A | 2/1999 |

(Continued)

OTHER PUBLICATIONS

Dec. 16, 2020 Extended Search Report issued in European Patent Application No. Application No. 18780391.1.
(Continued)

*Primary Examiner* — Anthony D Barfield
(74) *Attorney, Agent, or Firm* — Oliff PLC

(57) ABSTRACT

An arrangement structure for a biological sensor includes a biological sensor of a non-contact type provided in a seat on which a human is seated. The biological sensor detecting biological information of the human with electromagnetic waves. The biological sensor is arranged at a position in the seat avoiding a member that constitutes the seat and interferes with passage of the electromagnetic waves.

16 Claims, 19 Drawing Sheets

(51) Int. Cl.
  *A61B 5/024*    (2006.01)
  *A61B 5/026*    (2006.01)
  *A61B 5/1455*    (2006.01)
  *A61B 5/00*    (2006.01)

(52) U.S. Cl.
  CPC ........ *A61B 5/02444* (2013.01); *A61B 5/1455* (2013.01); *A61B 5/6893* (2013.01); *A61B 5/721* (2013.01)

(56) References Cited

U.S. PATENT DOCUMENTS

| | | | |
|---|---|---|---|
| 2010/0109390 A1 | 5/2010 | Nishimura et al. | |
| 2014/0276090 A1 | 9/2014 | Breed | |
| 2017/0057542 A1* | 3/2017 | Kim ................ | B60W 10/20 |

FOREIGN PATENT DOCUMENTS

| | | |
|---|---|---|
| JP | 2004-242945 A | 9/2004 |
| JP | 2009-055997 A | 3/2009 |
| JP | 2010-039633 A | 2/2010 |
| JP | 2015-96383 A | 5/2015 |
| JP | 2015-123359 A | 7/2015 |
| JP | 2016-106808 A | 6/2016 |
| JP | 2016-144989 A | 8/2016 |
| JP | 2016-168177 A | 9/2016 |
| JP | 2016-198121 A | 12/2016 |
| WO | 2015/002076 A1 | 1/2015 |
| WO | 2015/046055 A1 | 4/2015 |

OTHER PUBLICATIONS

Nov. 24, 2021 Office Action issued in Japanese Patent Application No. 2018-085928.
Dec. 14, 2021 Office Action issued in Japanese Patent Application No. 2018-070548.
Oct. 8, 2019 International Preliminary Report on Patentability issued in International Patent Application No. PCT/JP2018/014243.
Sep. 21, 2021 Office Action issued in Japanese Patent Application No. 2017-156696.
Aug. 4, 2021 Office Action issued in Chinese patent Application No. 201880023761.5.
Feb. 24, 2021 Office Action and Search Report issued in Japanese Patent Application No. 2017-156696.
May 29, 2018 International Search Report issued in International Application No. PCT/JP2018/014243.
Jan. 7, 2022 Office Action issued in Chinese Patent Application No. 201880023761.5.
Jun. 1, 2022 Office Action issued in Chinese Patent Application No. 201880023761.5.
Jul. 5, 2022 Office Action issued in Japanese Patent Application No. 2018-070548.
Aug. 2, 2022 Office Action issued in Japanese Patent Application No. 2018-101112.

* cited by examiner

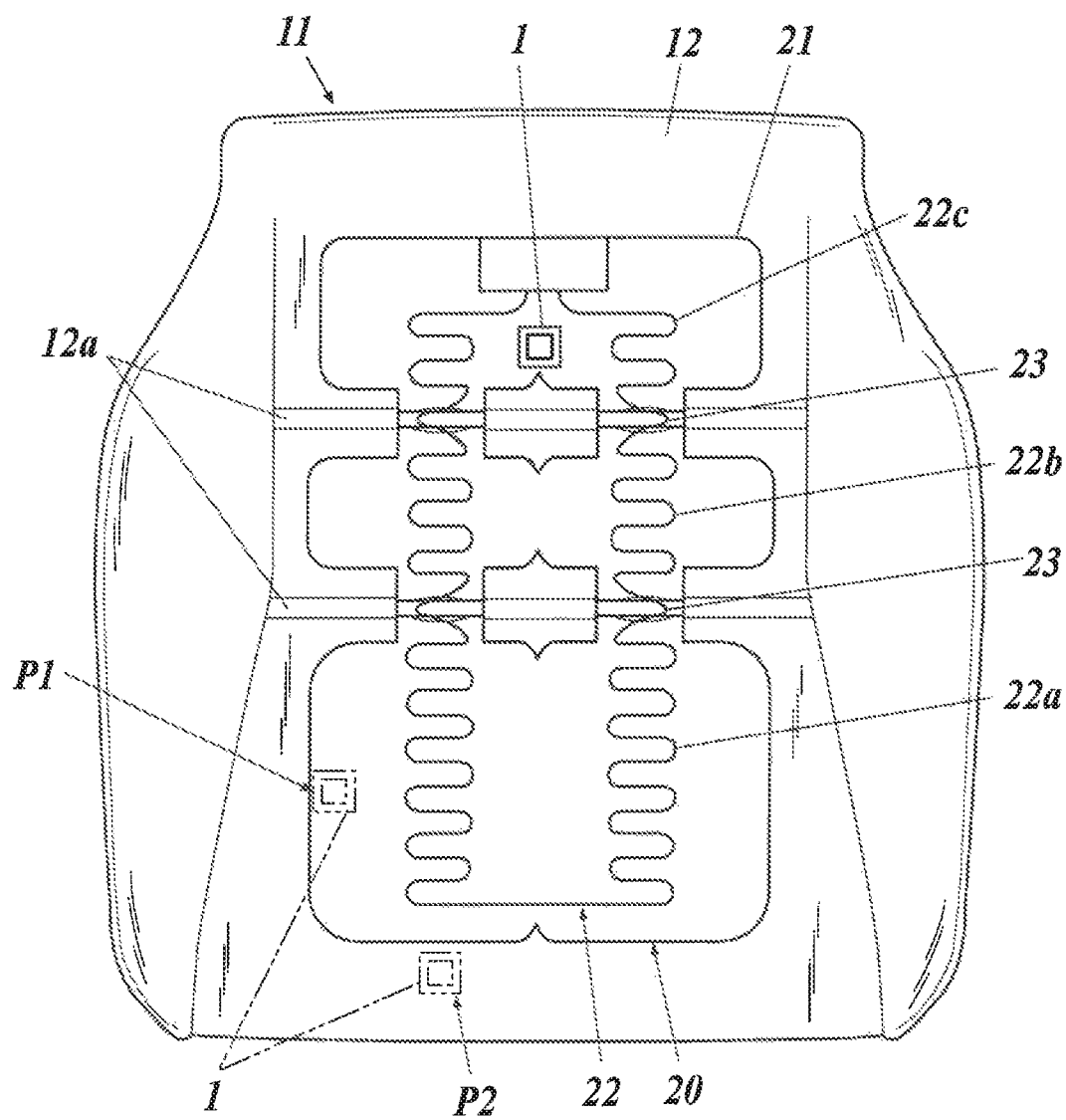
FIG.2
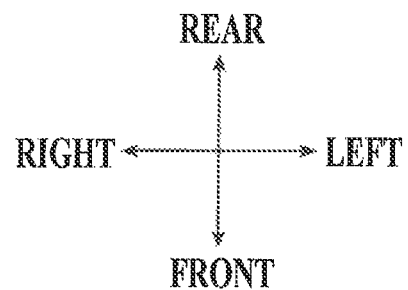

*FIG.3*
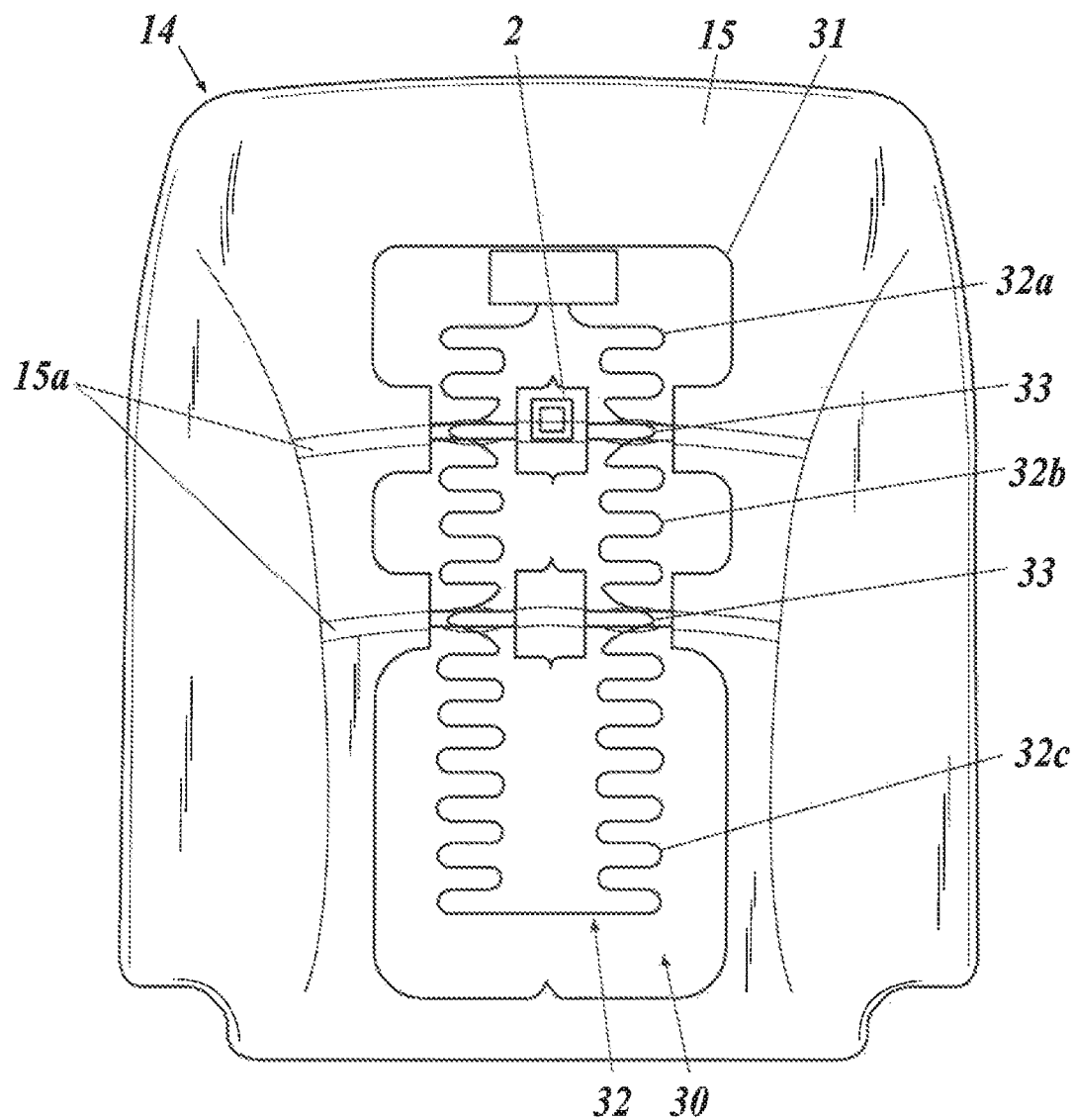
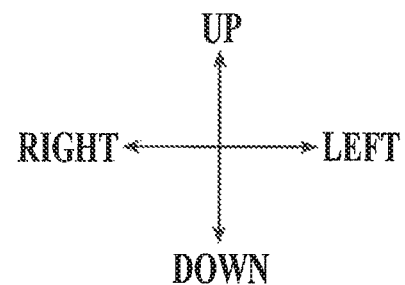

FIG.5
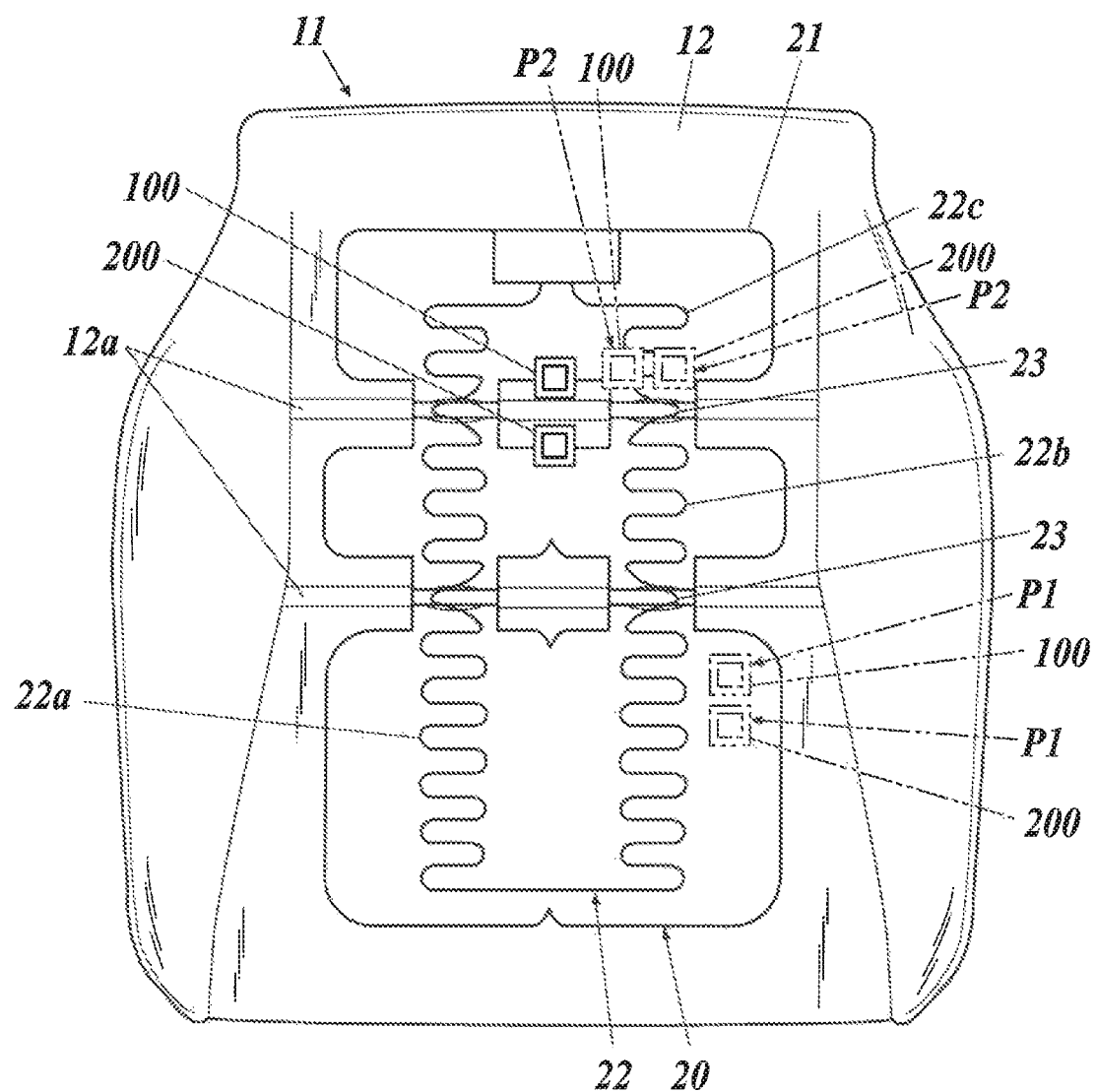
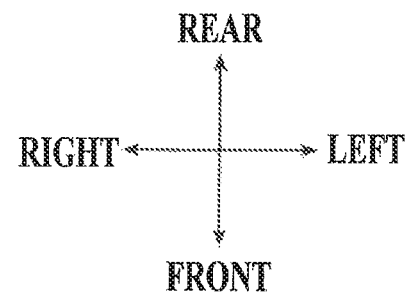

ARRANGEMENT STRUCTURE FOR BIOLOGICAL SENSORS

TECHNICAL FIELD

The present invention relates to an arrangement structure for a biological sensor.

BACKGROUND ART

When the health condition of the driver who is driving a vehicle deteriorates, it may adversely affect the driving of the vehicle. Therefore, it is desirable to detect the deterioration of the health condition in advance so that some measures can be taken. As for such measures, according to a known technique for grasping the health condition of the driver, biological information such as blood flow and blood pressure is estimated based on the measurement results of pulse waves and the like by a non-contact type blood flow sensor provided to be embedded in the surface to be seated and back of the seat (see Patent Literature 1).

CITATION LIST

Patent Literature

PTL 1: JP 2016-168177 A

SUMMARY OF INVENTION

Technical Problem

Biological sensors of a non-contact type are known to emit electromagnetic waves toward a living body and detect biological information based on the waves reflected by the living body. However, the electromagnetic waves emitted toward the living body are unlikely to pass through various metals such as iron, copper, and aluminum. For this reason, metal parts built in the seat may be interfere with electromagnetic waves from the biological sensor provided in the seat, which makes it difficult to accurately detect biological information.

The present invention has been made in consideration of the above problems, and an object of the present invention is to provide an arrangement structure for a biological sensor that makes it easy to accurately detect biological information.

Solution to Problem

In order to solve the above problems, according to the invention of claim 1, there is provided an arrangement structure for a biological sensor including:

a biological sensor of a non-contact type provided in a seat on which a human is seated, the biological sensor detecting biological information of the human with electromagnetic waves, and the biological sensor is arranged at a position in the seat avoiding a member that constitutes the seat and interferes with passage of the electromagnetic waves.

According to the invention of claim 2, in the arrangement structure for a biological sensor according to claim 1, the seat is provided in a vehicle that travels through autonomous driving or manual driving that are able to be switched to each other.

According to the invention of claim 3, in the arrangement structure for a biological sensor according to claim 1 or 2, the biological sensor arranged at the position in the seat emits electromagnetic waves whose emission center does not pass through the member.

According to the invention of claim 4, in the arrangement structure for a biological sensor according to claim 1 or 2, the biological sensor arranged at the position in the seat emits electromagnetic waves whose emission range does not include the member.

According to the invention of claim 5, in the arrangement structure for a biological sensor according to any one of claims 1 to 4, the biological sensor is arranged at the position in the seat closer to the human than the member is.

According to the invention of claim 6, the arrangement structure for a biological sensor according to claim 5 further includes:

a resin installation plate that is attached to the member and that is arranged at a position closer to the human than the member is, and the biological sensor is arranged on the installation plate.

According to the invention of claim 7, in the arrangement structure for a biological sensor according to any one of claims 1 to 4, the member has an opening, and the biological sensor is arranged at the position farther from the human than the member is, the position corresponding to a position of the opening.

According to the invention of claim 8, in the arrangement structure for a biological sensor according to any one of claims 1 to 7, the member is arranged so as not to be uniform in density inside the seat, and the biological sensor is arranged at a portion where density of the member is low.

According to the invention of claim 9, in the arrangement structure for a biological sensor according to any one of claims 1 to 8, the seat includes a cushion pad that is covered by a covering, and when a detachable portion of the cushion pad is detached, a recess that accommodates the biological sensor is formed inside the cushion pad.

According to the invention of claim 10, in the arrangement structure for a biological sensor according to any one of claims 1 to 8, the seat includes a cushion pad that is covered by a covering, and the cushion pad is formed with the biological sensor embedded in the cushion pad.

According to the invention of claim 11, in the arrangement structure for a biological sensor according to any one of claims 1 to 10, the biological sensor includes two or more biological sensors that are arranged at at least two respective portions of the seat that are separate from each other.

According to the invention of claim 12, in the arrangement structure for a biological sensor according to claim 1, the biological sensor includes a first sensor and a second sensor that emit electromagnetic waves of different frequencies toward the human, and the first sensor and the second sensor are arranged adjacent to each other.

According to the invention of claim 13, in the arrangement structure for a biological sensor according to claim 12, the biological sensor includes two or more biological sensors that are arranged at at least two respective portions of the seat that are separate from each other.

According to the invention of claim 14, in the arrangement structure for a biological sensor according to claim 12, the seat includes a seat cushion and a seat back, the seat cushion supporting a human buttock and a human thigh, and the seat back having a lower edge that is supported by the seat cushion, the biological sensor is provided in at least one of the seat cushion and the seat back, and the first sensor and the second sensor are arranged adjacent to each other in a surface direction of a surface to be seated of the seat.

According to the invention of claim 15, in the arrangement structure for a biological sensor according to claim 12, the seat includes a seat cushion and a seat back, the seat cushion supporting a human buttock and a human thigh, and the seat back having a lower edge supported by the seat cushion, the biological sensor is provided in at least one of the seat cushion and the seat back, and the first sensor and the second sensor are arranged adjacent to each other in a thickness direction of either the seat cushion or the seat back.

Advantageous Effects of Invention

According to the invention of claim 1, the biological sensor is arranged at a position in the seat avoiding a member that constitutes the seat and interferes with passage of the electromagnetic waves. Therefore, the member interfering with the passage of electromagnetic waves are less likely to interfere with the emission of electromagnetic waves from the biological sensor. This makes it easy to accurately detect biological information.

According to the invention of claim 2, because the seat is provided in a vehicle that travels through autonomous driving or manual driving that are able to be switched to each other, biological information of the driver seated on the seat can be detected. As a result, for example, when the driver's health condition deteriorates, the deterioration can be detected in advance, so that safety can be improved during autonomous driving and during manual driving.

According to the invention of claim 3, the biological sensor arranged at the position in the seat emits electromagnetic waves whose emission center does not pass through the member interfering with the passage of electromagnetic waves. Therefore, the biological sensor can detect biological information while being affected by the member interfering with the passage of electromagnetic waves.

According to the invention of claim 4, the biological sensor arranged at the position in the seat emits electromagnetic waves whose emission range does not include the member interfering with the passage of electromagnetic waves. Therefore, the biological sensor can detect biological information without being affected by the member interfering with the passage of electromagnetic waves.

According to the invention of claim 5, the biological sensor is arranged at the position in the seat closer to the human than the member is. Therefore, the biological sensor is less likely to be affected by the member interfering with the passage of electromagnetic waves.

According to the invention of claim 6, a resin installation plate is attached to the member and is arranged at a position closer to the human than the member is, and the biological sensor is arranged on the installation plate. Therefore, even if the biological sensor is arranged in the vicinity of the member interfering with the passage of the electromagnetic waves, the biological sensor is not easily affected by the member interfering with the passage of the electromagnetic waves.

According to the invention of claim 7, the biological sensor is arranged at the position farther from the human than the member interfering with the passage of the electromagnetic waves is, and the position corresponds to a position of the opening formed in the member interfering with the passage of the electromagnetic waves. Therefore, even though the biological sensor is arranged at a position farther from the human than the member interfering with the passage of electromagnetic waves is arranged in the seat, the biological sensor is not easily affected by the member interfering with the passage of the electromagnetic waves.

According to the invention of claim 8, the member interfering with the passage of the electromagnetic waves is arranged so as not to be uniform in density inside the seat, and the biological sensor is arranged at a portion where density of the member interfering with the passage of the electromagnetic waves is low. Therefore, compared with the case where the biological sensor is arranged at a portion where the density of the member interfering with the passage of electromagnetic waves is high, the biological sensor is not easily affected by the member interfering with the passage of the electromagnetic waves.

According to the invention of claim 9, the seat includes a cushion pad that is covered by a covering, and a recess that accommodates the biological sensor is formed inside the cushion pad when a detachable portion of the cushion pad is detached. Therefore, a space where the biological sensor is arranged can be secured in the seat.

According to the invention of claim 10, a cushion pad is formed in the seat with the biological sensor embedded therein. Therefore, installation of the seat can be efficiently performed with the biological sensor embedded in the cushion pad.

According to the invention of claim 11, the biological sensor includes two or more biological sensors that are arranged at at least two respective portions of the seat that are separate from each other. Therefore, human health condition can be calculated from the detected biological information with higher accuracy.

According to the invention of claim 12, among a first sensor and a second sensor included in the biological sensor, one is used to detect biological information including noise, and another is used for to detect noise. Therefore, only the biological information can be extracted by subtraction of the noise. Furthermore, because the first sensor and the second sensor are arranged adjacent to each other, there is little detection error between the first sensor and the second sensor. Therefore, it is easy to accurately detect biological information.

According to the invention of claim 13, biological information can be detected from at least two portions of the human body. Therefore, the human health condition can be calculated from the detected biological information with higher accuracy.

According to the invention of claim 14, because the biological sensor is provided at at least one of the seat cushion and the seat back, biological information can be detected from at least one of the upper side and the lower side of the human body.

Furthermore, because the first sensor and the second sensor are arranged adjacent to each other in the surface direction on the surface to be seated of the seat, the first sensor and the second sensor can be arranged adjacent to each other in the front-rear direction, up-down direction, left-right direction, or oblique direction, in consideration of, for example, the internal structure of the seat cushion or the seat back, the sitting comfort of the seat, and the like.

According to the invention of claim 15, because the biological sensor is provided at at least one of the seat cushion and the seat back, biological information can be detected from at least one of the upper side and the lower side of the human body.

Furthermore, because the first sensor and the second sensor are arranged adjacent to each other in the thickness direction of at least one of the seat cushion and the seat back, the first sensor and the second sensor can be arranged adjacent to each other even when it is difficult to arrange them adjacent to each other in the surface direction.

BRIEF DESCRIPTION OF DRAWINGS

FIG. 2 is a plan view showing of a seat cushion according to the first embodiment.

FIG. 3 is a plan view showing of a seat back according to the first embodiment.

FIG. 5 is a plan view showing of a seat cushion according to the second embodiment.

DESCRIPTION OF EMBODIMENTS

Hereinafter, embodiments of the present invention will be described with reference to the drawings. Although a variety of limitations that are technically favorable for carrying out the present invention are described in the following embodiments, the scope of the present invention is not limited to the following embodiments or illustrated examples.

First Embodiment

Figure 1:
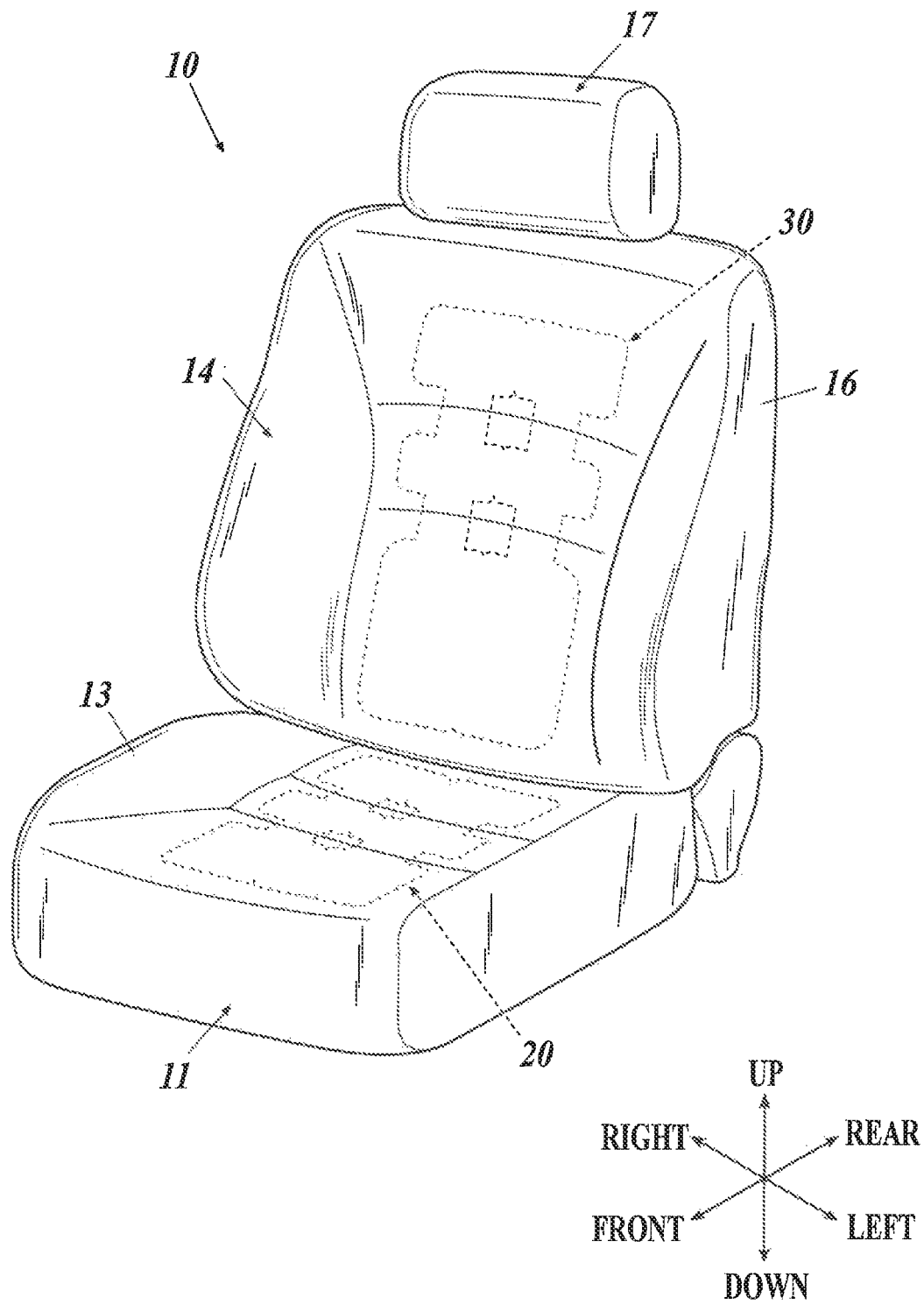
FIG. 1 is a perspective view of a seat with a built-in seat heater.

In FIG. 1, the numeral 10 denotes a seat on which a human is seated. This seat 10 is provided in a vehicle such as an automobile. In the present embodiment, the seat 10 is particularly provided in a vehicle capable of traveling through either one of autonomous driving and manual driving. The autonomous driving and manual driving can be switched to each other during the travel.

The seat 10 includes a seat cushion 11 supporting buttocks and thighs of the human, a seat back 14 having a lower edge supported by the seat cushion 11 and serves as a backrest, and a headrest 17 supporting the human head and provided on the seat back 14.

The main components of the seat cushion 11 include a seat cushion frame serving as a skeleton, a cushion pad 12 provided on the seat cushion frame, and a covering 13 covering the seat cushion frame and the cushion pad 12 (see FIG. 2). The seat cushion 11 of the present embodiment further includes a seat heater 20 provided between the cushion pad 12 and the covering 13.

Grooves 12a which are long in the left-right direction of the seat 10 are formed on the upper surface of the cushion pad 12. Two grooves 12a are formed on the upper surface of the cushion pad 12 and divide the upper surface of the cushion pad 12 into the front-rear direction. That is, the upper surface of the cushion pad 12 is divided into a front part, a center part, and a rear part.

The main components of the seat back 14 include a seat back frame serving as a skeleton, a cushion pad 15 provided on the seat back frame, and a covering 16 covering the seat back frame and the cushion pad 15 (see FIG. 3).

The seat back 14 of the present embodiment further includes a seat heater 30 provided between the cushion pad 15 and the covering 16.

Grooves 15a which are long in the left-right direction of the seat 10 are formed on the front surface of the cushion pad 15. Two grooves 15a are formed on the front surface of the cushion pad 15 and divide the front surface of the cushion pad 15 into the up-down direction. That is, the upper surface of the cushion pad 15 is divided into an upper part, a center part, and a lower part.

The seat heater 20 in the seat cushion 11 is a planar heating element that warms the seat cushion 11. As shown in FIG. 2, the main components of the seat heater 20 includes a planar base material 21 made of a polyester cloth material and the like, and a heater wire 22 (also referred to as electrically-heated wire) made of metal bonded and fixed to the base material 21.

As shown in FIG. 2, the heater wire 22 bonded and fixed on the base member 21 includes two heater wires 22 each meandering in parallel from the rear to the front of the seat cushion 11. The front portions of the respective heater wires 22 are connected to each other.

Although the heater wires 22 of the present embodiment meander in parallel in the front-rear direction and are fixed on the base material 21, the arrangement of the heater wires 22 is not limited thereto and may be changed as appropriate. Although the heater wires 22 are fixed on the base material 21 with an adhesive, the heater wires 22 may be folded inside the base material 21 to be fixed.

As shown in FIG. 2, each of the heater wires 22 includes a front heater wire 22a in a section of the front part on the upper surface of the cushion pad 12, a central heater wire 22b in a section of the center part, a rear heater wire 22c in a section of the rear part, and groove heater wires 23 which are inserted into the respective grooves 12a and connect the front heater wire 22a, the central heater wire 22b, and the rear heater wire 22c.

The seat heater 30 in the seat back 14 similarly includes a base material 31 and a heater wire 32 as main components.

As shown in FIG. 3, each of the heater wires 32 includes an upper heater wire 32a in a section of the upper part on the front surface of the cushion pad 15, a central heater wire 32b in a section of the center part, a lower heater wire 32c in a section of the lower part, and groove heater wires 33 which connect the upper heater wire 32a, the central heater wire 32b, and the lower heater wire 32c and are inserted into the respective grooves 15a.

As described above, because such a seat 10 is provided in a vehicle which can travel through either of autonomous driving and manual driving which can be switched to each other, the form inappropriate for manual driving and a form appropriate for manual driving can be changed to each other.

During autonomous driving, since the driver is allowed to be in a relaxed condition, the seat 10 is also changed to a form inappropriate for manual driving. For example, the seat 10 during autonomous driving can change its position so as to face the rear seat or so as to be in a flat condition.

Furthermore, although not shown in the drawings, such a vehicle includes a driving controller which switches between autonomous driving and manual driving, the above-described seat 10 which can be changed into a plurality of forms, and a seat controller which controls the operation of the seat 10 when changing the form.

When the vehicle on a highway moves to an ordinary road, or when the vehicle is approaching a road having a complicated shape, the driving controller controls the switch of autonomous driving to manual driving. If there is abnormality in the driver's health condition in such a case, forcible switching of autonomous driving to manual driving is not preferable. On the other hand, if the driver's health condition has become worse during manual driving, manual driving may be switched to autonomous driving. In such a case, the health condition needs to be grasped in advance.

Therefore, the seat 10 is provided with a biological sensor 1, 2 as a means for grasping the health condition of a driver, as shown in FIGS. 2 and 3. The biological sensor 1, 2 in the present embodiment measures the blood flow condition of a measurement target human, for example, measures the blood flow at positions facing the skin surface of the measurement target region.

The biological sensor 1, 2 of the present embodiment is of a non-contact type which detects human biological information using an electromagnetic wave(s), and is connected to the driving controller so that data communication is possible.

The driving controller switches between autonomous driving and manual driving based on the data related to biological information transmitted from the biological sensor 1, 2, and the seat controller changes the form of the seat 10 as appropriate.

The biological sensor 1, 2 in the present embodiment detects human biological information using electromagnetic waves as described above.

Here, electromagnetic waves mean electromagnetic waves in a broad sense including radiowaves of about 100 MHz, microwaves, infrared light, visible light, ultraviolet light, X-rays, and the like. Any suitable electromagnetic waves may be used as long as it does not adversely affect the human body.

Such electromagnetic waves have a feature that they do not easily pass through various metals such as iron, copper, and aluminum. Therefore, in the present embodiment shown in FIG. 4, the biological sensor 1, 2 is arranged at a position in the seat 10 avoiding the member A1, A2 (possibly) interfering with the passage of electromagnetic waves.

Figure 4:
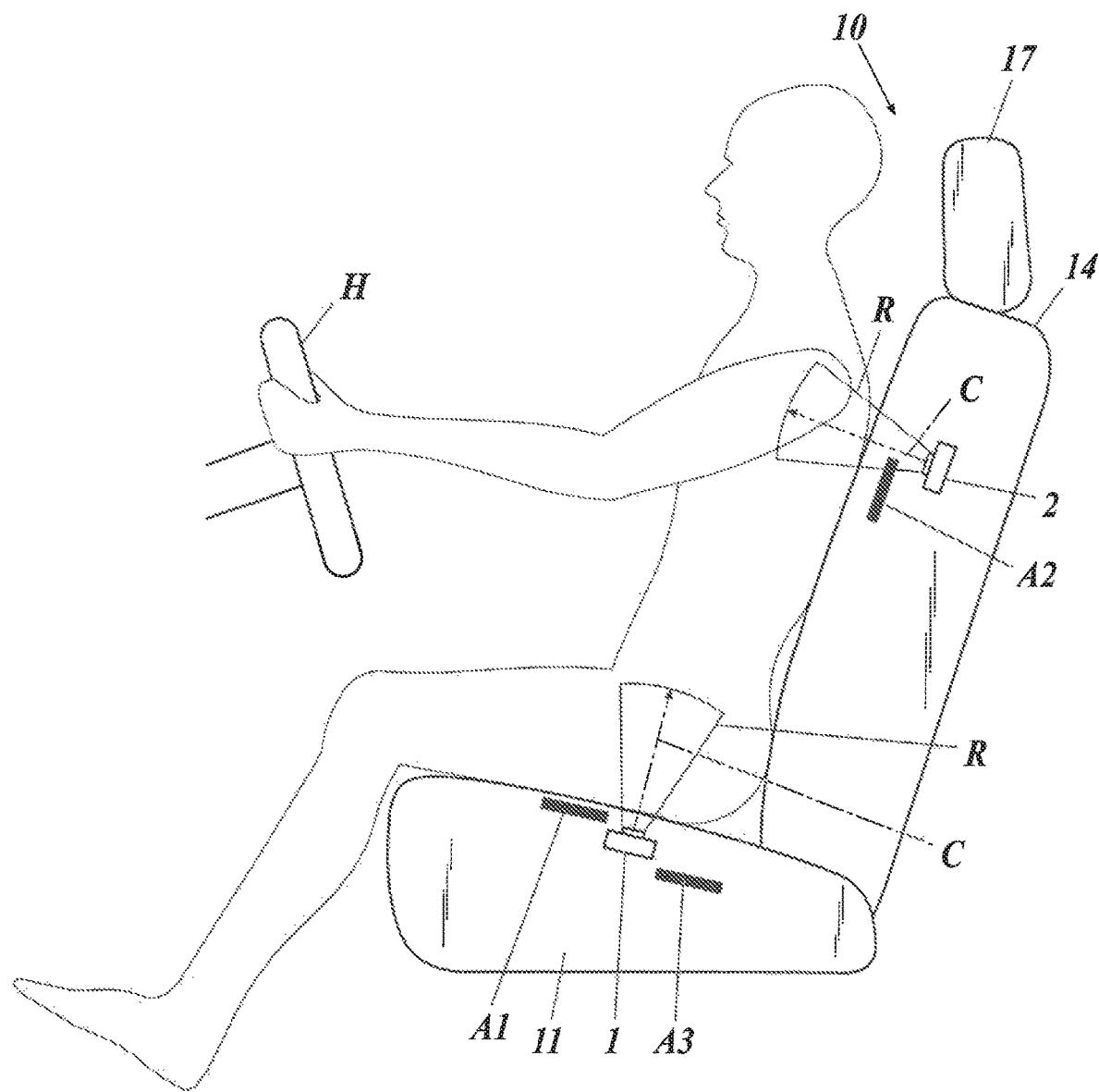
FIG. 4 is a diagram illustrating a positional relationship between an electromagnetic wave and a member that interferes with the electromagnetic wave in the first embodiment.

In the example shown in FIG. 4, the biological sensor 1 provided at the seat cushion 11 is arranged in the seat 10 at a position such that the member A1 does not overlap the emission range R of electromagnetic waves emitted from the biological sensor 1.

That is, when the biological sensor 1 is provided in the seat 10, a condition for accurately detecting biological information is that the interfering member A1 does not overlap the electromagnetic wave emission range R from the biological sensor 1.

In the example shown in FIG. 4, the biological sensor 2 provided at the seat back 14 is arranged in the seat 10 at a position such that an emission center C of the electromagnetic waves emitted from the biological sensor 2 does not pass through the member A2.

That is, when the biological sensor 2 is provided in the seat 10, the interfering member A2 may overlap the emission range R, as long as the emission center C of the electromagnetic waves emitted from the biological sensor 2 does not pass through the interfering member A2. This is also a condition for easily detecting biological information.

In the example shown in FIG. 4, the biological sensor 1 is arranged at a position closer to the human than the member A3 interfering with the passage of electromagnetic waves is. That is, in the seat 10, the biological sensors 1 and 2 are preferably arranged at positions closer to the human than the members (for example, the member A3) interfering with the passage of electromagnetic waves are.

Biological information can be detected even when the interfering members A1 and A2 are arranged closer to the human than the biological sensor 1, 2 is, as described above. However, the biological sensor 1, 2 is desirably arranged closer to the human than the interfering member A1, A2 is, because the interfering member A1, A2 is naturally less likely to interfere with the electromagnetic waves. This is also the condition for accurately detecting biological information.

The members A1, A2, and A3 interfering with the passage of electromagnetic waves are arranged at different relative positions with respect to the biological sensors 1 and 2, but the members A1, A2, and A3 may be arranged at any of the relative positions because none of them completely interfere with the passage of electromagnetic waves. However, if more accurate detection of biological information is required, the relative position of the member A3 is the most preferable, and the relative position of the member A1 is also preferable. The relative position of the member A2 is not unacceptable.

FIG. 4 is an example of the seat 10 viewed from the lateral side. As a supplementary explanation, even if the members A1, A2, and A3 are each in a relative position near the biological sensors 1 and 2 when viewed from the lateral side, they do not interfere with the passage of electromagnetic waves when arranged at different positions in the horizontal direction (left-right direction). Such a relative position is also preferred.

More specifically, the members A1, A2, and A3 interfering with the passage of electromagnetic waves in the present embodiment are metal heater wires 22 and 32 of the seat heaters 20 and 30 respectively shown in FIGS. 2 and 3. The biological sensors 1 and 2 are arranged in the seat 10 at positions avoiding the heater wires 22 and 32, respectively.

The biological sensors 1 and 2 are arranged at at least two respective portions of the seat 10 which are separate from each other. More specifically, both of the seat cushion 11 and the seat back 14 includes the biological sensors 1 and 2.

As shown in FIG. 2, the biological sensor 1 provided in the seat cushion 11 is arranged at a portion corresponding to the middle portion of the left and right sciatic bones of human buttocks so that sitting comfort is improved. In other words, the biological sensor 1 is arranged in the middle of the position where the buttocks are mounted in the seat cushion 11.

In the present embodiment, the biological sensor 1 is arranged so as to correspond to the middle portion of the left and right sciatic bones, but is not limited thereto. For example, the biological sensor 1 provided in the seat cushion 11 may be arranged corresponding to the positions of femurs.

That is, reference numerals P1 and P2 in FIG. 2 are candidate portions for arranging the biological sensor 1, and the candidate portions P1 and P2 correspond to the positions of the femurs of the human seated on the seat 10.

The femurs in which popliteal arteries pass are suitable for measurement of blood flow conditions with the biological sensor 1.

As shown in FIG. 3, the biological sensor 2 provided in the seat back 14 is arranged at a portion corresponding to the position of the human heart. The chest where the heart is present and through which thoracic aorta passes is suitable for measurement of blood flow conditions with the biological sensor 2.

In other words, the heater wires 32 of the seat heater 30 provided in the seat back 14 are arranged avoiding the position of the human heart so that the measurement accuracy is improved with the biological sensor 2 arranged at the human heart position. That is, the heater wires 32 (22) interfering with the passage of electromagnetic waves are arranged so as not to be uniform in density inside the seat 10, and the biological sensor 2 is arranged at a portion where the density of the heater wires 32 (22) are low (sparse). The higher the density of the heater wires 32 (22) is, the higher temperature it becomes.

In the present embodiment, the biological sensor 2 is arranged at a portion corresponding to the heart position, but is not limited thereto. The biological sensor 2 may be at any position suitable for measurement of the blood flow condition.

The pulse wave velocity and the degree of arteriosclerosis can be determined using data relating to the blood flow condition(s) in the popliteal artery and the thoracic aorta obtained by measurement with the biological sensor 1, 2. Here, a calculation program incorporated in advance in the above driving controller (or another external device such as a computer) is used. Furthermore, on the basis of the pulse wave velocity and the degree of arteriosclerosis, the driving controller can calculate the blood pressure (arterial pressure) of the human who is the measurement target human.

As described above, the seat 10 in the present embodiment is provided in a vehicle capable of travelling through either of autonomous driving and manual driving which can be switched to each other. Therefore, in order to improve safety, the biological sensor 1, 2 may be used in combination with a camera (not shown) that captures the human sitting on the seat 10. When the biological sensor 1, 2 is used in combination with a camera, it can be determined whether or not the human who is seated but does not put his hand(s) on the steering wheel H is deteriorating in human health, as well as whether or not he is just asleep.

Furthermore, the biological sensor 1, 2 may be used in combination with a microphone which collects the voice of the human seated on the seat 10 to confirm whether or not the human is conscious. That is, if the human seated on the seat 10 is urged to speak but does not make a response, it is determined that the driver is unconscious.

According to the present embodiment as described above, the biological sensor 1, 2 is arranged in the seat 10 at a position avoiding the member A1, A2, A3 interfering with the passage of electromagnetic waves among the members constituting the seat 10. Therefore, the member A1, A2, A3 interfering with the passage of electromagnetic waves is less likely to interfere with the emission of electromagnetic waves from the biological sensor 1, 2. This makes it easy to accurately detect biological information.

Furthermore, because the seat 10 is provided in a vehicle capable of travelling through either of autonomous driving and manual driving which can be switched to each other, the biological information of the driver seated on the seat can be detected. As a result, for example, when the driver's health condition deteriorates, the deterioration can be detected in advance, so that safety can be improved during autonomous driving and during manual driving.

Furthermore, because the biological sensor 2 is arranged in the seat 10 at a position such that emission center C of the electromagnetic waves emitted from the biological sensor 2 do not pass through the member A2 interfering with the passage of electromagnetic waves, the biological sensor 2 can detect biological information while being affected by the member A2 interfering with the passage of electromagnetic waves.

Furthermore, because the biological sensor 1 is arranged in the seat 10 at a position such that the member does not overlap the emission range R of the electromagnetic waves emitted from the biological sensor 1, the biological sensor 1 can detect biological information without being affected by the member A1, A3 interfering with the passage of electromagnetic waves.

Furthermore, because the biological sensor 1 is arranged in the seat 10 at a position closer to the human than the member A3 interfering with the passage of electromagnetic waves is, the biological sensor 1 is less likely to be affected by the member A3 interfering with the passage of electromagnetic waves.

Furthermore, when the biological sensors 1 and 2 are arranged at at least two respective portions of the seat which are separate from each other, biological information can be detected from at least two portions of the human body. As a result, the human health condition can be calculated from the detected biological information with higher accuracy.

Furthermore, when the seat cushion 11 and the seat back 14 respectively include the biological sensors 1 and 2, biological information can be detected from the upper side and the lower side of the human body. As a result, the human health condition can be calculated from the detected biological information with higher accuracy.

Furthermore, because the biological sensor 2 provided in the seat back 14 is arranged corresponding to the human heart position, blood flow conditions can be grasped from the thoracic aorta. In such a case, biological information can be detected more easily than the case from thin blood vessels with less blood flow.

Furthermore, because the biological sensor 1 provided in the seat cushion 11 is arranged at a portion corresponding to the middle portion of the left and right sciatic bones of the human buttocks, the biological sensor 1 can be arranged so as not to knock the sciatic bones, such that the comfort when the human is seated on the seat is not impaired.

Furthermore, because the biological sensor 1 provided in the seat cushion 11 is arranged at a portion corresponding to the position of the thighs, the blood flow condition of the popliteal arteries can be grasped. In such a case, biological information can be detected more easily than in the case of thin blood vessels with less blood flow.

Second Embodiment

The seat 10 (see FIG. 1) in the present embodiment is provided in a vehicle such as an automobile. The vehicle may be one capable of traveling only through manual driving, or through either one of autonomous driving and manual driving which can be switched to each other.

The seat 10 includes a seat cushion 11 which supports the human buttocks and thighs, a seat back 14 which has a lower edge supported by the seat cushion 11 and serves as a backrest, and a headrest 17 which supports the human head and provided on the seat back 14.

The main components of the seat cushion 11 include a seat cushion frame serving as a skeleton, a cushion pad 12 provided on the seat cushion frame, and a covering 13 covering the seat cushion frame and the cushion pad 12 (see FIG. 5). The seat cushion 11 of the present embodiment further includes a seat heater 20 provided between the cushion pad 12 and the covering 13.

Grooves 12a which are long in the left-right direction of the seat 10 are formed on the upper surface of the cushion pad 12. Two grooves 12a are formed on the upper surface of the cushion pad 12 and divide the upper surface of the cushion pad 12 into the front-rear direction. That is, the upper surface of the cushion pad 12 is divided into a front part, a center part, and a rear part.

Figure 6:
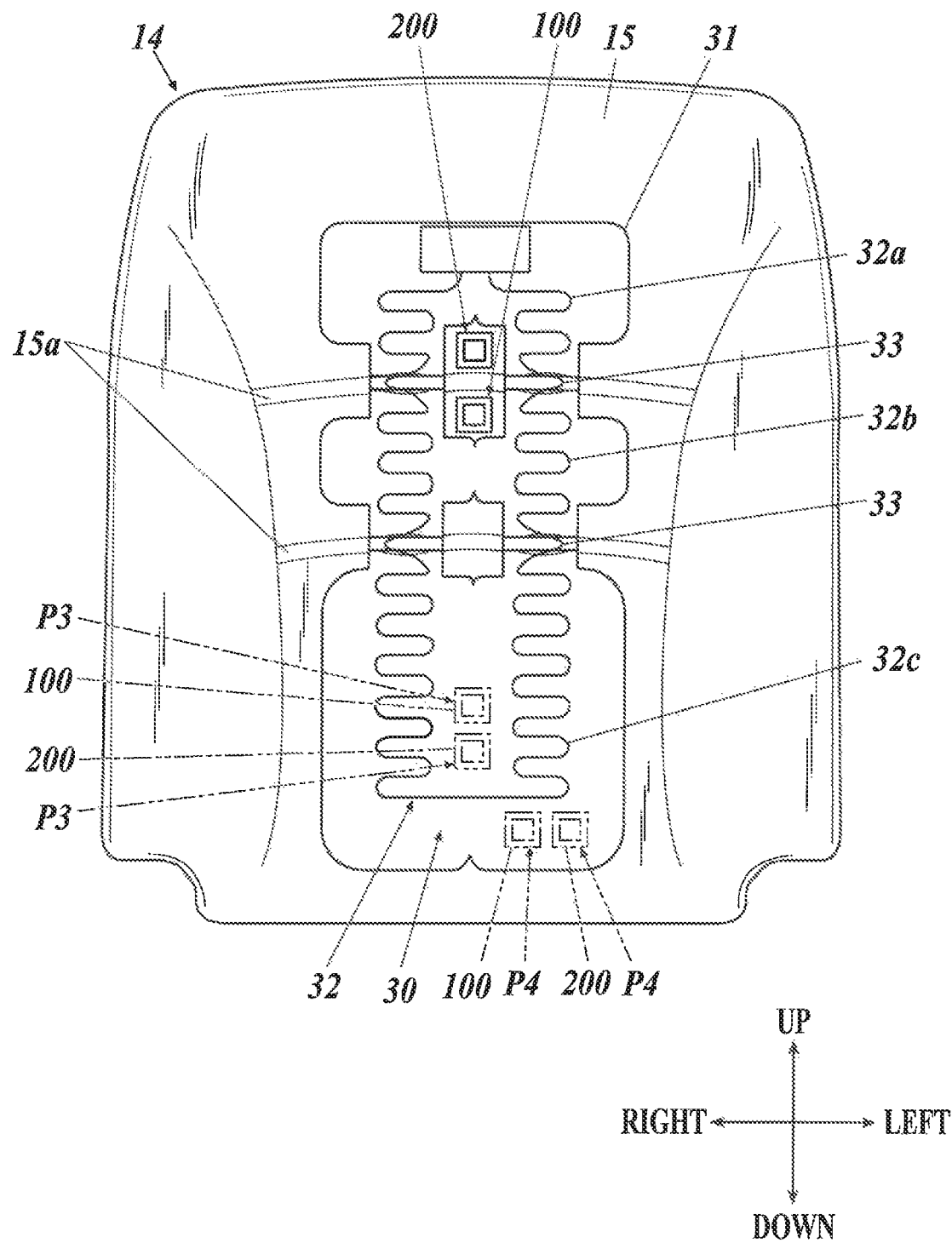
FIG. 6 is a plan view showing of a seat back according to the second embodiment.

The main components of the seat back 14 include a seat back frame serving as a skeleton, a cushion pad 15 provided on the seat back frame, and a covering 16 that covers the seat back frame and the cushion pad 15 (see FIG. 6).

The seat back 14 of the present embodiment further includes a seat heater 30 provided between the cushion pad 15 and the covering 16.

Grooves 15a which are long in the left-right direction of the seat 10 are formed on the front surface of the cushion pad 15. Two grooves 15a are formed on the front surface of the cushion pad 15 and divide the front surface of the cushion pad 15 into the up-down direction. That is, the upper surface of the cushion pad 15 is divided into an upper part, a center part, and a lower part.

The seat heater 20 in the seat cushion 11 is a planar heating element that warms the seat cushion 11. As shown in FIG. 5, the main components of the seat heater 20 includes a planar base material 21 made of a polyester cloth material and the like, and a heater wire 22 (also referred to as electrically-heated wire) made of metal bonded and fixed to the base material 21.

As shown in FIG. 5, the heater wire 22 bonded and fixed on the base member 21 includes two heater wires 22 each meandering in parallel from the rear to the front of the seat cushion 11. The front portions of the respective heater wires 22 are connected to each other.

Although the heater wires 22 of the present embodiment meander in parallel in the front-rear direction and are fixed on the base material 21, the arrangement of the heater wires 22 is not limited thereto and may be changed as appropriate. Although the heater wires 22 are fixed on the base material 21 with an adhesive, the heater wires 22 may be folded inside the base material 21 to be fixed.

As shown in FIG. 5, each of the heater wires 22 includes a front heater wire 22a in a section of the front part on the upper surface of the cushion pad 12, a central heater wire 22b in a section of the center part, a rear heater wire 22c in a section of the rear part, and groove heater wires 23 which are inserted into the respective grooves 12a and connect the front heater wire 22a, the central heater wire 22b, and the rear heater wire 22c.

The seat heater 30 in the seat back 14 similarly includes a base material 31 and a heater wire 32 as main components.

As shown in FIG. 6, each of the heater wires 32 includes an upper heater wire 32a in a section of the upper part on the front surface of the cushion pad 15, a central heater wire 32b in a section of the center part, a lower heater wire 32c in a section of the lower part, and groove heater wires 33 which are inserted into the respective grooves 15a and connect the upper heater wire 32a, the central heater wire 32b, and the lower heater wire 32c.

If such a seat 10 is provided in a vehicle which can travel through either one of autonomous driving and manual driving which can be switched to each other, the driver is allowed to be in a relaxed condition during autonomous driving, and the seat 10 is changed to a form inappropriate for manual driving. For example, the seat 10 during autonomous driving can change its position so as to face the rear seat or so as to be in a flat condition.

Furthermore, if the seat 10 is provided in a vehicle which can travel only through manual driving, the seat 10 can be reclined when the vehicle stops.

Furthermore, although not shown in the drawings, a driving controller is included in the vehicle capable of traveling through either one of autonomous driving and manual driving which can be switched to each other. The driving controller switches between autonomous driving and manual driving, the above-described seat 10 can be changed into a plurality of forms, and the seat controller controls the operation of the seat 10 when changing the form.

When the vehicle on a highway moves to an ordinary road, or when the vehicle is approaching a road having a complicated shape, the driving controller controls the switch of autonomous driving to manual driving. If there is abnormality in the driver's health condition in such a case, forcible switching of autonomous driving to manual driving is not preferable. On the other hand, if the driver's health condition has become worse during manual driving, manual driving may be switched to autonomous driving. In such a case, the health condition needs to be grasped in advance.

When the vehicle is capable of traveling through manual driving only, the seat controller may also control the movement of the seat 10 automatically when the vehicle stops. The health condition may be grasped when the vehicle stops.

For convenience of explanation, the vehicle in the following is capable of traveling through either one of autonomous driving and manual driving which can be switched to each other, but the present invention is not limited thereto. The vehicle may be capable of traveling only through manual driving.

The seat 10 is provided with a biological sensor(s) 100, 200 as a means for grasping the health condition of a driver, as shown in FIGS. 5 and 6. The biological sensor 100, 200 in the present embodiment is used for measuring the blood flow condition of a measurement target human, for example, and can measure the blood flow at positions facing the skin surface of the measurement target region.

The biological sensor 100, 200 of the present embodiment is of a non-contact type for detecting human biological information using electromagnetic waves, and is connected to the driving controller so that data communication is possible.

The driving controller switches between autonomous driving and manual driving based on the data related to biological information transmitted from the biological sensor 100, 200, and the seat controller changes the form of the seat 10 as appropriate.

The biological sensor 100, 200 of the present embodiment is of a non-contact type for detecting human biological information using electromagnetic waves, and is connected to the driving controller so that data communication is possible.

The driving controller switches between autonomous driving and manual driving based on the data related to biological information transmitted from the biological sensor 100, 200, and the seat controller changes the form of the seat 10 as appropriate.

The biological sensor 100, 200 in the present embodiment detects human biological information using electromagnetic waves as described above.

More specifically, the biological sensor 100, 200 in the present embodiment includes a first sensor 100 and a second sensor 200 which emit electromagnetic waves of different frequencies toward the human. The first sensor 100 and the second sensor 200 basically have a function of detecting minute vibrations of the body surface due to pulsation based on reflection of electromagnetic waves emitted to the human body. The first sensor 100 and the second sensor 200 are also called Doppler sensors because they use the frequency shifts of the reflected wave due to the Doppler Effect depending on the speed of an object. Since such a Doppler sensor also detects slight body movements during breathing etc., body movements other than pulse wave may be detected as noise component (s). However, such noise can be removed by using the first sensor 100 and the second sensor 200, and only the pulse wave can be extracted.

The first sensor 100 is a biological sensor which emits electromagnetic waves of a frequency to reach the blood. A biological sensor which emits electromagnetic waves capable of reaching the blood makes use of a change in reflectance of the electromagnetic waves depending on the amount of hemoglobin in the blood. Hemoglobin transports oxygen throughout the body. Oxygen deficiency in the tissue (cells) causes symptoms such as rapid blood flow for quick transport of oxygen (palpitations) and rapid breathing for uptake of a large amount of oxygen into the body (shortness of breath). The first sensor 100 can detect such body conditions (blood flow condition: pulse wave).

The first sensor 100 detects minute vibrations of the body surface when the amount of hemoglobin is detected. That is, the waveform of detection data obtained by the first sensor 100 represents both a pulse wave and noise.

The frequency of the electromagnetic wave reaching the blood is, for example, 270 MHz, but is not particularly limited as long as it can reach the blood to detect the amount of hemoglobin.

Further, the first sensor 100 is integrated with a receiver that receives reflected waves of the electromagnetic waves emitted by the first sensor 100. That is, the first sensor 100 has both an emission function for emitting electromagnetic waves and a reception function for receiving electromagnetic waves.

The receiver is connected to a calculation unit (not shown) (included in the driving controller in the present embodiment) so that data communication is possible. The data regarding the detected pulse wave and noise is sent to and stored in the calculation unit.

The second sensor 200 is a biological sensor which emits electromagnetic waves having a frequency for detecting minute vibrations of the body surface. The second sensor 200 can detect only minute vibrations of the body surface, that is, noise. That is, the waveform of detection data obtained by the second sensor 200 represents noise only.

The frequency of the electromagnetic waves for detecting minute vibrations of the body surface is, for example, 10 GHz, but is not particularly limited as long as it can detect the minute vibrations of the body surface.

Furthermore, the second sensor 200 is integrated with a receiver that receives reflected waves of the electromagnetic waves emitted by the second sensor 200. That is, the second sensor 200 has both an emission function for emitting electromagnetic waves and a reception function for receiving electromagnetic waves.

The receiver is connected to a calculation unit (not shown, included in the driving controller in the present embodiment) so that data communication is possible. The data regarding the detected noise is sent to and stored in the calculation unit.

The first sensor 100 detects the pulse wave and noise, and the second sensor 200 detects the noise. Therefore, only the pulse wave can be extracted by subtraction of the noise.

If the first sensor 100 and the second sensor 200 are arranged at a large interval, their noise may not correspond to each other (an error occurs). Therefore, the first sensor 100 and the second sensor 200 are arranged adjacent to each other. That is, the first sensor 100 and the second sensor 200 are arranged as close as possible to each other or arranged so as to contact each other.

The biological sensor 100, 200 in the present embodiment detects human biological information using electromagnetic waves as described above.

Such electromagnetic waves have a feature that they do not easily pass through various metals such as iron, copper, and aluminum. Therefore, in the present embodiment shown in FIG. 7, the biological sensors 100, 200 are arranged at positions avoiding the members A1 to A3 (possibly) interfering with the passage of electromagnetic waves with respect to the seat 10.

Figure 7:
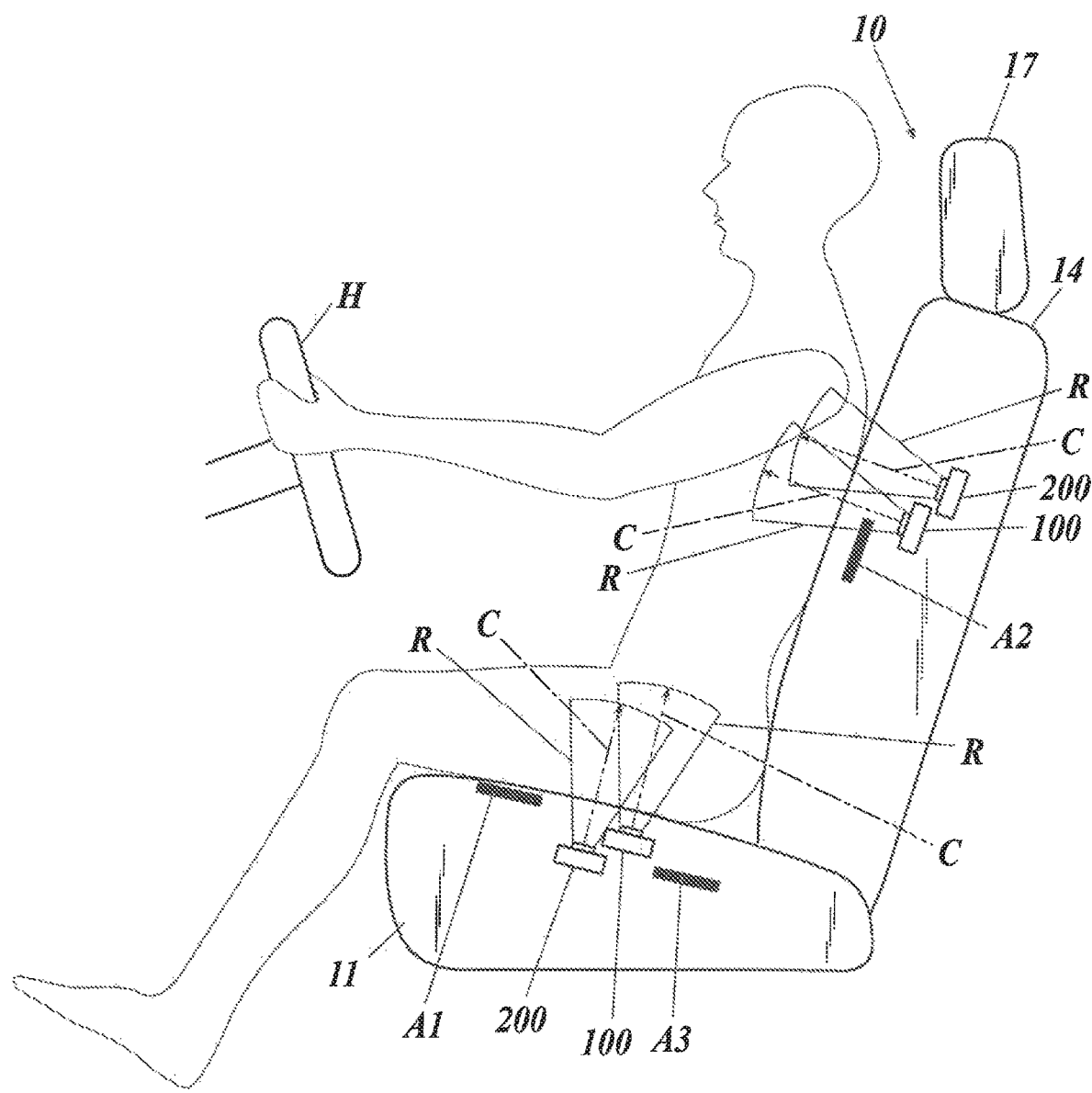
FIG. 7 is a diagram illustrating a positional relationship between an electromagnetic wave and a member that interferes with the electromagnetic wave in the second embodiment.

In the example shown in FIG. 7, the first sensor 100 and the second sensor 200 provided in the seat cushion 11 are arranged at respective positions in the seat 10 such that the member A1 does not overlap the electromagnetic wave emission range R from the first sensor 100 or the second sensor 200.

That is, when the first sensor 100 and the second sensor 200 are provided in the seat 10, the interfering member A1 does not overlap the electromagnetic wave emission ranges R from the first sensor 100 and the second sensor 200, which is also the condition for accurately detecting biological information.

In the example shown in FIG. 7, the first sensor 100 and the second sensor 200 provided in the seat back 14 are arranged in the seat 10 at respective positions such that the emission center C of the electromagnetic waves emitted from the first sensor 100 or the second sensor 200 does not pass through the member A2.

That is, when the first sensor 100 and the second sensor 200 are provided in the seat 10, the interfering member A2 may overlap the emission ranges R as long as the emission centers C of the first sensor 100 and the second sensor 200 do not pass through the interfering member A2. This is also a condition for easily detecting biological information.

In the example shown in FIG. 7, the first sensor 100 and the second sensor 200 are arranged at respective positions closer to the human than the member A3 interfering with the passage of electromagnetic waves is. That is, in the seat 10, the first sensor 100 and the second sensor 200 are preferably arranged at positions closer to the human than the member (for example, the member A3) interfering with the passage of electromagnetic waves is.

Biological information can be detected even when the interfering members A1 and A2 are arranged closer to the human than the first sensors 100 and the second sensors 200 are, as described above. However, the first sensors 100 and the second sensors 200 are desirably arranged closer to the human than the interfering members A1 and A2 are, because the interfering members A1 and A2 are naturally less likely to interfere with the electromagnetic waves. This is also the condition for accurately detecting biological information.

The members A1, A2, and A3 interfering with the passage of electromagnetic waves have different relative positions with respect to the first sensors 100 and the second sensors 200, but the members A1, A2, and A3 may be at any of the relative positions because none of them completely interfere with the passage of electromagnetic waves. However, if more accurate detection of biological information is required, the relative position of the member A3 is the most preferable, and the relative position of the member A1 is also preferable. The relative position of the member A2 is not unacceptable.

FIG. 7 is an example of the seat 10 viewed from the lateral side. As a supplementary explanation, even if the members A1, A2, and A3 are each in a relative position near the biological sensor 100, 200 when viewed from the lateral side, they do not interfere with the passage of electromagnetic waves when arranged at different positions in the horizontal direction (left-right direction). Such a relative position is also preferred.

Furthermore, the first sensor 100 and the second sensor 200 are arranged adjacent to each other as described above, which is also the condition for accurately detecting biological information.

Therefore, the first sensor 100 and the second sensor 200 are arranged adjacent to each other in the surface direction on the surface to be seated of the seat 10. In the present embodiment, the first sensor 100 and the second sensor 200 have an electromagnetic waves emission surface arranged in parallel or substantially parallel to the surface to be seated of the seat 10.

In the case of the seat cushion 11 in FIG. 5, the surface to be seated of the seat 10 refers to a surface in contact with human buttocks and thighs. In the case of the seat back 14 in FIG. 6, the surface to be seated of the seat 10 refers to a surface in contact with the human back (chest side, lumbar side). In the case of the seat cushion 11, the first sensor 100 and the second sensor 200 are arranged adjacent to each other in the front-rear direction, the left-right direction, or the oblique direction. In the case of the seat back 14, the first sensor 100 and the second sensor 200 are arranged adjacent to each other in the up-down direction, the left-right direction, or the oblique direction.

Furthermore, as shown in FIG. 7, the first sensor 100 and the second sensor 200 may be arranged adjacent to each other in the thickness direction of at least one of the seat cushion 11 and the seat back 14. In this case, the first sensor 100 and the second sensor 200 may be arranged so as to partially overlap each other.

As described above, when the first sensor 100 and the second sensor 200 are arranged adjacent to each other in the thickness direction of at least one of the seat cushion 11 and the seat back 14, the first sensor 100 which emits electromagnetic waves of a frequency to reach the blood is preferably arranged on the side of the surface to be seated (front side), and the second sensor 200 which emits electromagnetic waves having a frequency for detecting minute vibrations of the body surface is preferably arranged on the side away from the surface to be seated (rear side), so that the emission distances of electromagnetic waves are equivalent.

The arrangement of the first sensor 100 and the second sensor 200 is now described more specifically. the members A1, A2, and A3 interfering with the passage of electromagnetic waves in the present embodiment are metal heater wires 22 and 32 of the seat heaters 20 and 30 respectively shown in FIGS. 5 and 6. The first sensor 100 and the second sensor 2 are arranged in the seat 10 at positions avoiding the heater wires 22 and 32.

The first sensor 100 and the second sensor 200 are arranged at each of at least two portions of the seat 10 which are separate from each other. More specifically, the first sensor 100 and second sensor 200 are provided in each of the seat cushion 11 and the seat back 14.

As described above, when the first sensor 100 and the second sensor 200 are arranged at each of at least two portions of the seat 10 which are separate from each other, the distances from the position of the heart of the human seated on the seat 10 (the position where the heart is estimated to be present) to each of the at least two portions provided with the biological sensor 100, 200 can be calculated. As a result, pulse waves can be preferably detected.

It is necessary for calculation of the blood pressure of a measurement target human to consider the length of the artery. However, since there are individual differences in the human body, pulse waves are detected with the seat 10 as a reference as described above.

Furthermore, in order that the length of the artery is easily discriminated and the accuracy of pulse wave detection is improved, the at least two portions provided with the biological sensor 100, 200 may be limited to be in the seat cushion 11 only or in the seat back 14 only. When the biological sensor 100, 200 is arranged at at least two portions of the seat cushion 11, it is preferably arranged along either the left or right thigh. When the biological sensor 100, 200 is arranged at at least two respective portions of the seat back 14, it may be arranged in either the left side or right side of the spine or arranged along the spine, with the position (center) of the spine avoided.

As shown in FIG. 5, the first sensor 100 and the second sensor 200 in the seat cushion 11 are provided along the center of the surface to be seated of the seat cushion 11 so that sitting comfort can be improved. That is, they are arranged at portions corresponding to the middle portion (gluteal cleft) of the left and right sciatic bones of human buttocks. In other words, the first sensor 100 and the second sensor 200 are arranged at the middle of the respective positions where the buttocks are mounted in the seat cushion 11 in the seat 10.

In the present embodiment, the first sensor 100 and the second sensor 200 are arranged corresponding to the middle portion of the left and right sciatic bones, but is not limited thereto. For example, as indicated by two-dot chain lines in FIG. 5, the first sensor 100 and the second sensor 200 provided in the seat cushion 11 may be arranged corresponding to the positions of human femurs.

That is, reference numerals P1 and P2 in FIG. 5 are candidate portions for arranging the first sensor 100 and the second sensor 200. The candidate portion P1 corresponds to the position of the femur of the human seated on the seat 10, and the candidate portion P2 corresponds to the position of the left sciatic bone of the human buttocks.

The femur in which popliteal arteries pass is suitable for measurement of blood flow conditions with the biological sensor 100, 200.

As shown in FIG. 6, the first sensor 100 and the second sensor 200 provided in the seat back 14 are arranged along the center of the surface to be seated of the seat 10, corresponding to the human heart position. The chest where the heart is present and through which thoracic aorta passes is suitable for measurement of blood flow conditions with the first sensor 100 and the second sensor 200.

In other words, the heater wires 32 of the seat heater 30 provided in the seat back 14 are arranged avoiding the position of the human heart so that the measurement accuracy is improved with the first sensor 100 and the second sensor 200 each arranged at the human heart position. That is, the heater wires 32 (22) interfering with the passage of electromagnetic waves are arranged so as not to be uniform in density inside the seat 10, and the first sensor 100 and the second sensor 200 are arranged at portions where the density of the heater wires 32 (22) are low (sparse). The higher the density of the heater wires 32 (22) is, the higher temperature it becomes. However, if the first sensor 100 and the second sensor 200 are arranged closer to the surface to be seated than the heater wire 32 (22) is, a problem is unlikely to occur in the detection of biological information.

In the present embodiment, the first sensor 100 and the second sensor 200 are arranged at portions each corresponding to the position of the heart, but are not limited thereto. The first sensor 100 and the second sensor 200 may be at any position suitable for measurement of the blood flow condition. For example, as indicated by two-dot chain lines in FIG. 6, the first sensor 100 and the second sensor 200 may be arranged at portions each corresponding to the center position of the human lumbar region or at portions corresponding to either left or right of the human lumbar region.

That is, reference numerals P3 and P4 in FIG. 6 are candidate portions for arranging the first sensor 100 and the second sensor 200. The candidate portion P3 corresponds to the center position of a lumbar region of the human seated on the seat 10, and the candidate portion P4 corresponds to the left position of the lumbar region of the human.

As described above, Doppler sensors such as the first sensor 100 and the second sensor 200 also detect slight body movements. Therefore, the first sensor 100 and the second sensor 200 are each arranged at a portion corresponding to the body portion with little movement in the human seated on the seat 10, such as buttocks, thighs, or lumbar region. If it is determined that the position of the heart is preferable even if there are many body movements, the first sensor 100 and the second sensor 200 are arranged corresponding to the position of the heart. In addition, although the thigh is a region with little body movement, the thigh in the leg that operates the accelerator or the brake may move a lot. Therefore, the first sensor 100 and the second sensor 200 are preferably arranged corresponding to the thigh in the leg which does not operate the accelerator or the brake.

Figure 14:
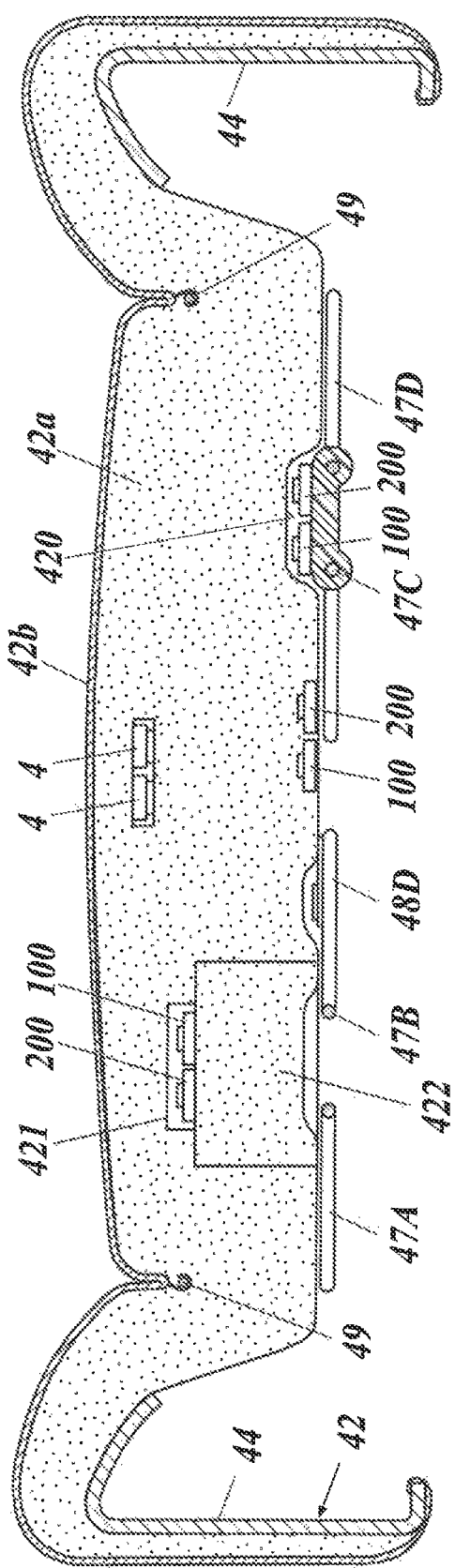
FIG. 14 is a cross-sectional view of a seat cushion including spring members built therein according to Modification 3.

Furthermore, at the position of the groove 12a in the cushion pad 12 of the seat cushion 11 and the position of the groove 15a in the cushion pad 15 of the seat back 14, there is provided a metal wire for forming suspending portions of the coverings 13 and 16 (see the suspending portions 49 in FIG. 14). The first sensor 100 and the second sensor 200 are arranged avoiding positions of the grooves 12a and 15a (that is, the suspending portions).

The pulse wave velocity and the degree of arteriosclerosis can be determined using data relating to the blood flow condition(s) in the popliteal artery and the thoracic aorta obtained by measurement with the first sensor 100 and the second sensor 200. Here, a calculation program incorporated in advance in the above driving controller (or another external device such as a computer) is used. Furthermore, on the basis of the pulse wave velocity and the degree of arteriosclerosis, the driving controller can calculate the blood pressure (arterial pressure) of the human who is the measurement target human. That is, the driving controller functions as the calculation unit described above.

As described above, the seat 10 in the present embodiment is provided in a vehicle capable of travelling through either one of autonomous driving and manual driving which can be switched to each other. Therefore, in order to improve safety, the first sensor 100 and the second sensor 200 may be used in combination with a camera (not shown) that captures the human sitting on the seat 10. When the first sensor 100 and the second sensor 200 are used in combination with a camera, it can be determined whether or not the human who is seated but does not put his hand(s) on the steering wheel H is deteriorating in his health, as well as whether or not he is just asleep.

Furthermore, the first sensor 100 and the second sensor 200 may be used in combination with a microphone which collects the voice of the human seated on the seat 10 to confirm whether or not the human is conscious. That is, if the human seated on the seat 10 is urged to speak but does not make a response, it is determined that the driver is unconscious.

According to the present embodiment as described above, one of the first sensor 100 and the second sensor 200 may be used for detection of biological information including noise, and the other is used for detection of noise. Therefore, only the biological information can be extracted by subtraction of the noise. Furthermore, because the first sensor 100 and the second sensor 200 are arranged adjacent to each other, there is little detection error between the first sensor 100 and the second sensor 200. Accordingly, it is easy to accurately detect biological information.

Furthermore, because biological information can be detected from at least two portions in the human body, human health condition can be calculated from the detected biological information with higher accuracy.

Furthermore, because at least one of the seat cushion 11 and the seat back 14 includes the biological sensor, biological information can be detected from at least one of the upper side and the lower side of the human body.

Furthermore, because the first sensor 100 and the second sensor 200 are arranged adjacent to each other in the surface direction on the surface to be seated of the seat 10, the first sensor 100 and the second sensor 200 can be arranged adjacent to each other in the front-rear direction, up-down direction, left-right direction, or oblique direction, in consideration of, for example, the internal structure of the seat cushion 11 or the seat back 14, the sitting comfort of the seat 10, and the like.

Furthermore, because the first sensor 100 and the second sensor 200 are arranged adjacent to each other in the thickness direction of at least one of the seat cushion 11 and the seat back 14, the first sensor 100 and the second sensor 200 can be arranged adjacent to each other even when it is difficult to arrange them adjacent to each other in the surface direction.

Furthermore, because the first sensor 100 and the second sensor 200 are arranged so as to partially overlap each other, the first sensor 100 and the second sensor 200 can be arranged adjacent to each other so as not to interfere with each other in detection of biological information.

Furthermore, if the biological sensor 100, 200 is provided along the center of the surface to be seated of the seat 10, the biological sensor 100, 200 is arranged along the gluteal cleft or spine. Therefore, the sitting comfort of the seat 10 would not be impaired.

If the biological sensor 100, 200 is provided on one side of the surface to be seated of the seat 10, the biological sensor 100, 200 is arranged avoiding the positions of the gluteal cleft and the spine. As a result, the distance between the human body and the biological sensor 100, 200 becomes short, so that biological information can be easily detected.

[Modifications]

The embodiments to which the present invention can be applied are not limited to the above-described embodiment, and the scope of the present invention can be suitably changed without leaving the scope of the invention. The modifications are described below. The modifications described below can be combined if possible.

[Modification 1]

Figure 8:
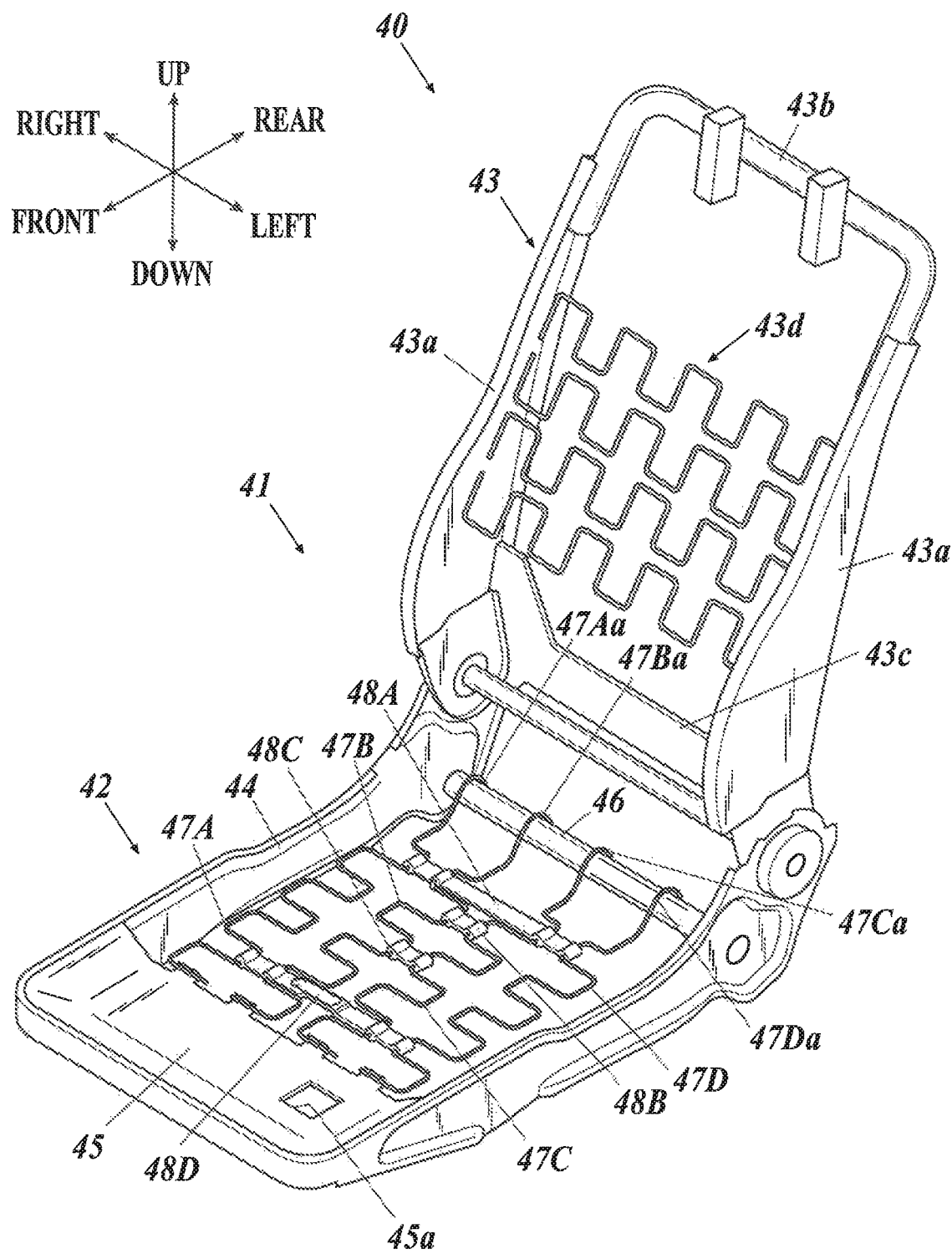
FIG. 8 is a perspective view showing a seat in which spring members are built in a seat cushion according to Modification 1.

The seat 40 in this modification includes a built-in seat frame 41 as shown in FIG. 8. The seat frame 41 includes a cushion frame 42 constituting a seat cushion and a seat back frame 43 constituting a seat back.

The cushion frame 42 and the seat back frame 43 are each provided with a cushion pad 42a and further covered with a covering 42b to constitute the seat 40.

The cushion frame 42 has a frame shape in a plan view and includes a pair of side frames 44, a pan frame 45, and a connecting pipe 46. The paired side frames 44 each extend long in the front-rear direction and are spaced separately in the left-right direction. The pan frame 45 is composed of a metal plate connecting the front edges of the paired side frames 44. The connection pipe 46 is formed of a metal pipe which connects the rear edges of the paired side frames 44.

A seat spring 47 is installed between the pan frame 45 and the connecting pipe 46.

The seat spring 47 includes four spring members 47A to 47D which extend long in the front-rear direction and are arranged in the left-right direction, and resin connection members 48A to 48D which connect the spring members 47A to 47D.

Each of the spring members 47A to 47D is a bending metal wire. The rear ends of the spring members 47A to 47D are respectively formed into hooks 47Aa to 47Da to be hooked to the connecting pipe 46. The spring members 47A to 47D respectively extend forward from the hooks 47Aa to 47Da each bending to the left and right directions to form zigzags. As shown in FIG. 8, the spring members 47A to 47D have respective front edges each connected to the pan frame 45 so as not to be displaced.

The biological sensor 1 is provided in the cushion frame 42. In the present modification, the spring members 47A to 47D are the members interfering with the passage of electromagnetic waves, and the biological sensor 1 is arranged at a position avoiding the spring members 47A to 47D.

Figure 9:
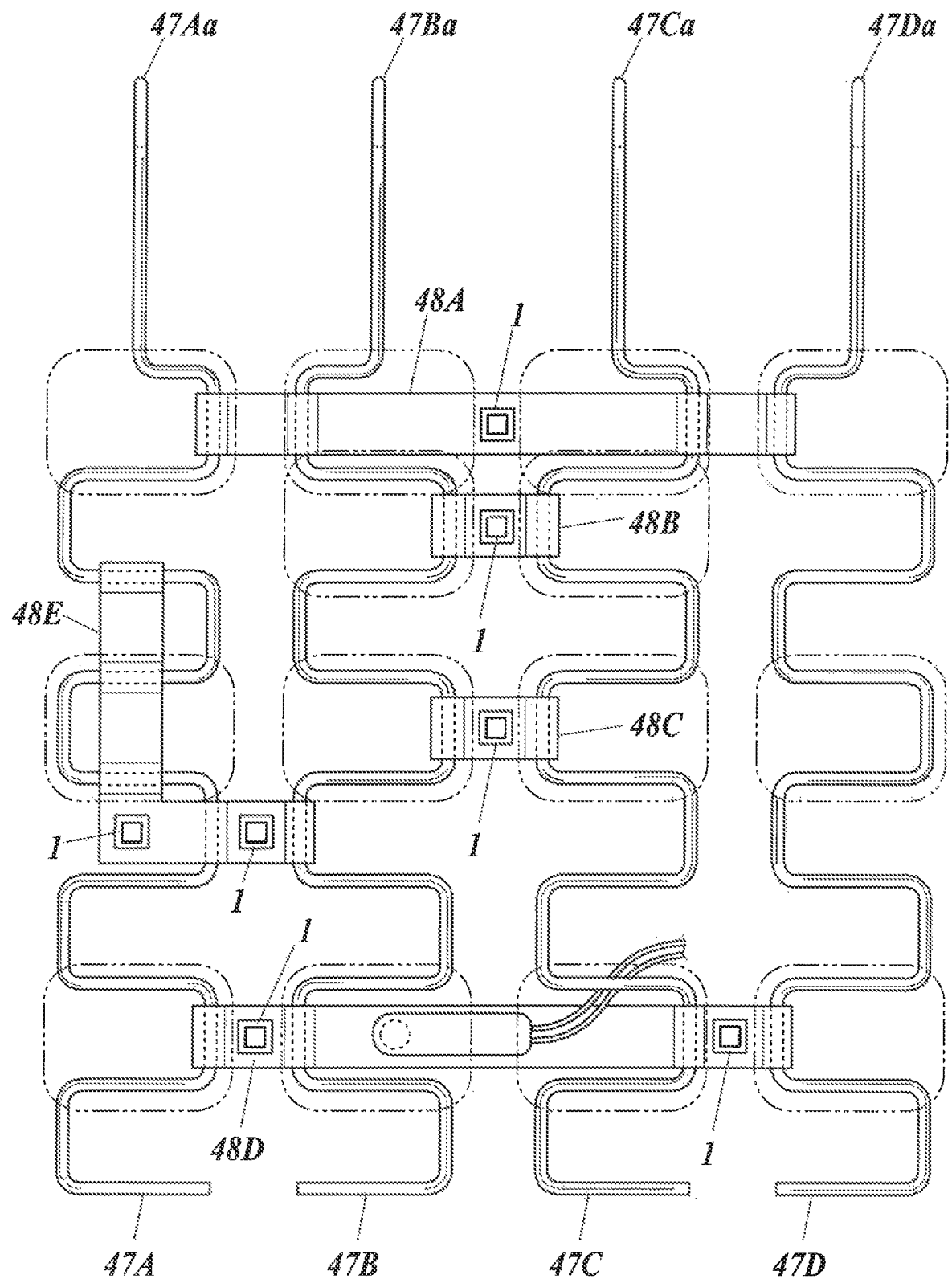
FIG. 9 is a plan view showing spring members according to Modification 1.

More specifically, the connecting members 48A to 48D are provided with biological sensor(s) 1 as shown in FIG. 9. The position(s) of the biological sensor(s) 1 correspond to the middle portion of the left and right sciatic bones of human buttocks or correspond to the position of the thigh. When the biological sensor(s) are provided at the portion(s) corresponding to the position of the thigh, the portion(s) may correspond to either one thigh or both thighs.

The connecting members 48A to 48D are arranged at positions closer to the human than the spring members 47A to 47D are. Since the biological sensor(s) 1 are provided on such connecting members 48A to 48D, the measurement results by the biological sensor(s) 1 are less affected by the spring members 47A to 47D.

The connecting members 48A to 48D are provided so as to connect the spring members 47A to 47D. However, as well as another connecting member 48E in FIG. 9, the zigzag portions of each of the spring members 47A to 47D each bending to form zigzags may be connected to each other. The another connecting member 48E has a portion that connects the adjacent spring members 47A and 47B and a portion that connects the zigzag portions of the spring member 47A, and is formed in a substantially L shape in a plan view. The biological sensor(s) 1 can be also arranged on such connecting member 48E.

In other words, the above-described connecting members 48A to 48E are installation plates each having a plate-shaped portion on whose upper surface the biological sensor(s) 1 are installed. That is, the biological sensor(s) 1 are arranged on the connecting members 48A to 48E as described above in the present modification, but are not limited thereto. A plate-like member which is located under the cushion pad 42a and on whose upper surface the biological sensor(s) 1 are installed (that is, an installation plate placed differently from the connecting members 48A to 48E) may be used.

Figure 10:
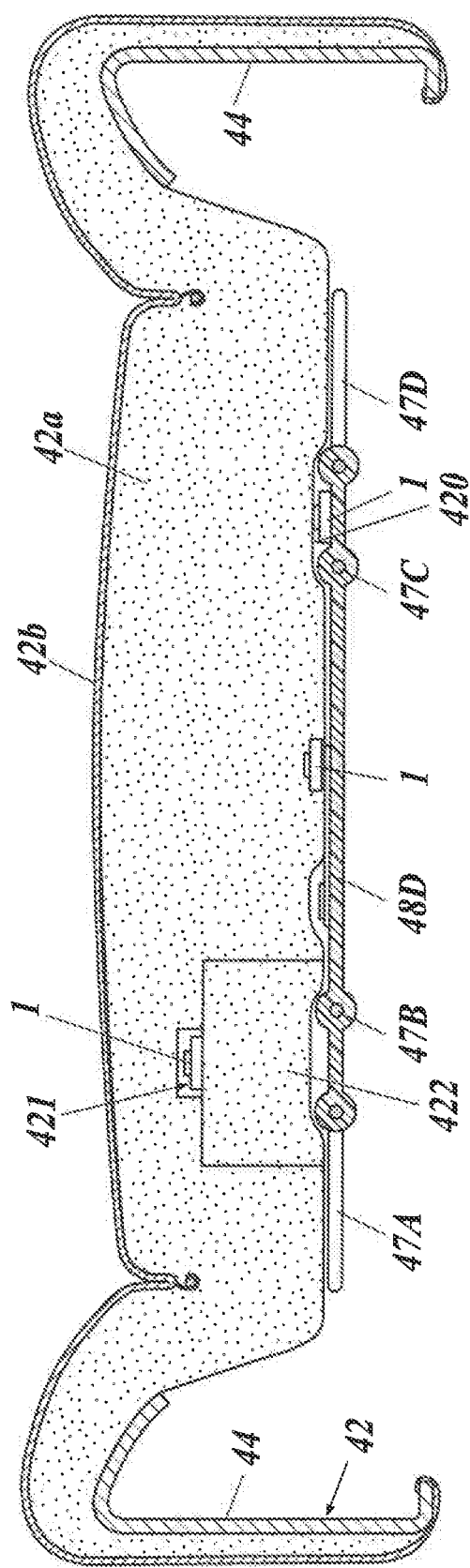
FIG. 10 is a cross-sectional view of a seat cushion including spring members built therein according to Modification 1.

As the biological sensor 1 may be disposed on each of the connecting members 48A to 48E, the cushion pad 42a of the seat 40 has a recess 420 which can accommodate the biological sensor 1 and which is formed at the portion located above the portion where the biological sensor 1 is installed. As shown in FIG. 10, the recess 420 is formed by recessing the lower surface of the cushion pad 42a.

Furthermore, because the spring members 47A to 47D have respective front edges each connected to the pan frame 45 so as not to be displaced as described above, the biological sensors 1 installed at the respective connecting members 48A to 48D can also be prevented from being displaced.

Furthermore, the biological sensor 1 may also be arranged on the pan frame 45. Since the pan frame 45 is a member made of metal plate as described above and interferes with the passage of electromagnetic waves, the biological sensor 1 is preferably arranged on the upper side of the pan frame 45. That is, the biological sensor 1 is arranged at a position closer to the human than a member (pan frame 45) interfering with the passage of electromagnetic waves is.

When arranged on the upper surface of the pan frame 45, the biological sensor 1 may be arranged either at a flat portion near the center or at an inclined portion near the periphery of the pan frame 45.

However, the biological sensor 1 may be arranged at a position farther from the human than the pan frame 4 is arranged, if it is arranged at a portion corresponding to an opening 45*a* formed in the pan frame 45 as shown in FIG. 8. By arranging the biological sensor 1 in this way, electromagnetic waves can be emitted toward the human through the opening 45*a*.

Furthermore, instead of the pan frame 45, the front edges of the paired side frames 44 may be connected to each other using a frame material or a pipe material (not shown). In this case, the front edges of the respective spring members 47A to 47D may be connected to the frame material or pipe material. The biological sensor 1 may be arranged with a clip or the like (not shown) on the frame material or the pipe material provided instead of the pan frame 45 as described above.

Furthermore, as shown in FIG. 10, the biological sensor(s) 1 may be provided so as to be embedded in the cushion pad 42*a* of the cushion frame 42. If the biological sensor 1 is provided so as to be embedded in the cushion pad 42*a*, the cushion pad 42*a* itself may be formed by so-called insert molding while the biological sensor 1 is embedded therein. If the biological sensor 1 is provided so as to be embedded in the cushion pad 42*a*, a recess (not shown) for accommodating the biological sensor 1 may be formed in the cushion pad 42*a* so that the biological sensor 1 can be easily installed.

The method for providing the biological sensor 1 so as to be embedded in the cushion pad 42*a* is not limited to the insert molding as described above. The biological sensor 1 is preferably embedded even after the cushion pad 42*a* has been molded. That is, a part of the cushion pad 42*a* (detachable portion 422 in FIG. 10) may be detachably formed, such that a recess 421 for accommodating the biological sensor 1 is formed at a position corresponding to the detachable portion 422.

If the biological sensor 1 is provided so as to be embedded in the cushion pad 42*a*, the detachable portion 422 is detached, the biological sensor 1 is accommodated in the recess 421, and the detachable portion 422 is returned to be fitted again. In this way, the biological sensor 1 can be embedded in the cushion pad 42*a*.

In the present modification, the detachable portion 422 can be detached from the lower surface side of the cushion pad 42*a*, but may be detached from the upper surface side.

There may be formed a space in the cushion pad 42*a* for wiring a harness (not shown) for electrically connecting the biological sensor 1 and an external device (for example, a power generation element, a storage, a control device, and the like), not only for embedding the biological sensor 1.

As shown in FIG. 8, the seat back frame 43 is provided with a pair of side frames 43*a*, an upper frame 43*b*, and a lower member 43*c*. The paired side frames 43*a* each extend long in the up-down direction and are spaced separately in the left-right direction. The upper frame 43*b* is provided between the upper edges of the paired side frames 43*a*. The lower member 43*c* is a plate like member provided between the lower edges of the paired side frames 43*a*. A seat spring 43*d* composed of multiple spring members is provided so as to link the paired side frames 43*a* between the upper frame 43*d* and the lower member 43*c*.

The multiple spring members of the seat spring 43*d* extend in the left-right direction and each bend up and down to form zigzags.

The biological sensor 2 can be also provided on the above-described seat back frame 43, as well as on the above-described cushion frame 42.

That is, the biological sensor 2 may be provided on either one or both of the paired side frames 43*a*. In that case, the biological sensor 2 may be attached to either the inner surface or the outer surface of the side frames 43*a*.

The biological sensor 2 may be provided on the front surface of the lower member 43*c*. When the biological sensor 2 is arranged on the rear surface side of the metal lower member 43*c*, the biological sensor 2 is arranged so as to correspond to the position of an opening (not shown) formed in the lower member 43*c*.

Furthermore, the biological sensor 2 may be provided on the seat spring 43*d*. In that case, as well as in the case on the above-described cushion frame 42, the biological sensor 2 may be arranged on the connection members (not shown) connecting the respective spring members of the seat spring 43*d*. Alternatively, if the spring members are not uniform in density, the biological sensor 2 may be arranged at a portion where the density of the spring members is low.

The biological sensor 2 may be embedded in a cushion pad (not shown) provided on the front surface side of the seat back frame 43, in the same way as the side of the above-described cushion frame 42.

According to the present modification, the biological sensor 1 is arranged in the seat 40 at a position avoiding the member(s) 47A to 47D interfering with the passage of electromagnetic waves among the members constituting the seat 40. Therefore, the member(s) 47A to 47D interfering with the passage of electromagnetic waves is less likely to interfere with the emission of electromagnetic waves from the biological sensor 1. This makes it easy to accurately detect biological information.

Furthermore, because the biological sensor 1 provided in the cushion frame 42 is arranged at a portion corresponding to the middle portion of the left and right sciatic bones of the human buttocks, the biological sensor 1 can be arranged so as not to knock the sciatic bones, such that the comfort when the human is seated on the seat is not impaired. Furthermore, because the biological sensor 1 provided in the cushion frame 42 is arranged at a portion corresponding to the position of the thighs, the blood flow condition of the popliteal arteries can be grasped. In such a case, biological information can be detected more easily than in the case of thin blood vessels with less blood flow.

Furthermore, a resin installation plate (connecting member(s) 48A to 48E) attached to the member(s) 47A to 47D and 43*d* interfering with the passage of electromagnetic waves are arranged at respective positions closer to the human than the member(s) 47A to 47D and 43*d* is. The biological sensor 1 (2) is arranged on the installation plate. Therefore, even if the biological sensor 1 (2) is arranged in the vicinity of the members 47A to 47D and 43*d* interfering with the passage of the electromagnetic waves, the biological sensor 1 (2) is not easily affected by the member (s) 47A to 47D and 43*d* interfering with the passage of the electromagnetic waves.

Furthermore, in the seat 40, the biological sensor 1, 2 is arranged at a position corresponding to the position of an opening 45a and farther from the human than the member (pan frame 45, lower member 43c) interfering with the passage of electromagnetic wave. The opening 45a is formed in the member 45, 43c interfering with the passage of electromagnetic waves. Therefore, even though the biological sensor 1, 2 is arranged at a position farther from the human than the member 45, 43c interfering with the passage of electromagnetic waves are arranged in the seat 40, the biological sensor 1, 2 is not easily affected by the member 45, 43c interfering with the passage of the electromagnetic waves.

In addition, the member(s) 47A to 47D and 43d interfering with the passage of electromagnetic waves are arranged inside the seat 40 so as not to be uniform in density, and the biological sensor 1, 2 is arranged at a portion where the density of the member(s) 47A to 47B interfering with the passage of electromagnetic waves is low. Therefore, compared with the case where the biological sensor 1, 2 is arranged at a portion where the density of the member(s) 47A to 47B interfering with the passage of electromagnetic waves is high, the biological sensor 1, 2 is not easily affected by the member(s) 47A to 47D and 43d interfering with the passage of the electromagnetic waves.

Furthermore, the cushion pad 42a in the seat 40 has a part (detachable portion 422) which is configured to be detachable, and includes a recess 421 which accommodates the biological sensor 1 at a position corresponding to the portion 422. Therefore, a space where the biological sensor 1 is arranged can be secured in the seat 40.

Furthermore, because the cushion pad 42a in the seat 40 is formed with the biological sensor 1 embedded therein, installation of the seat 40 can be efficiently performed with the biological sensor 1 embedded in the cushion pad 42a.

[Modification 2]

Figure 11:
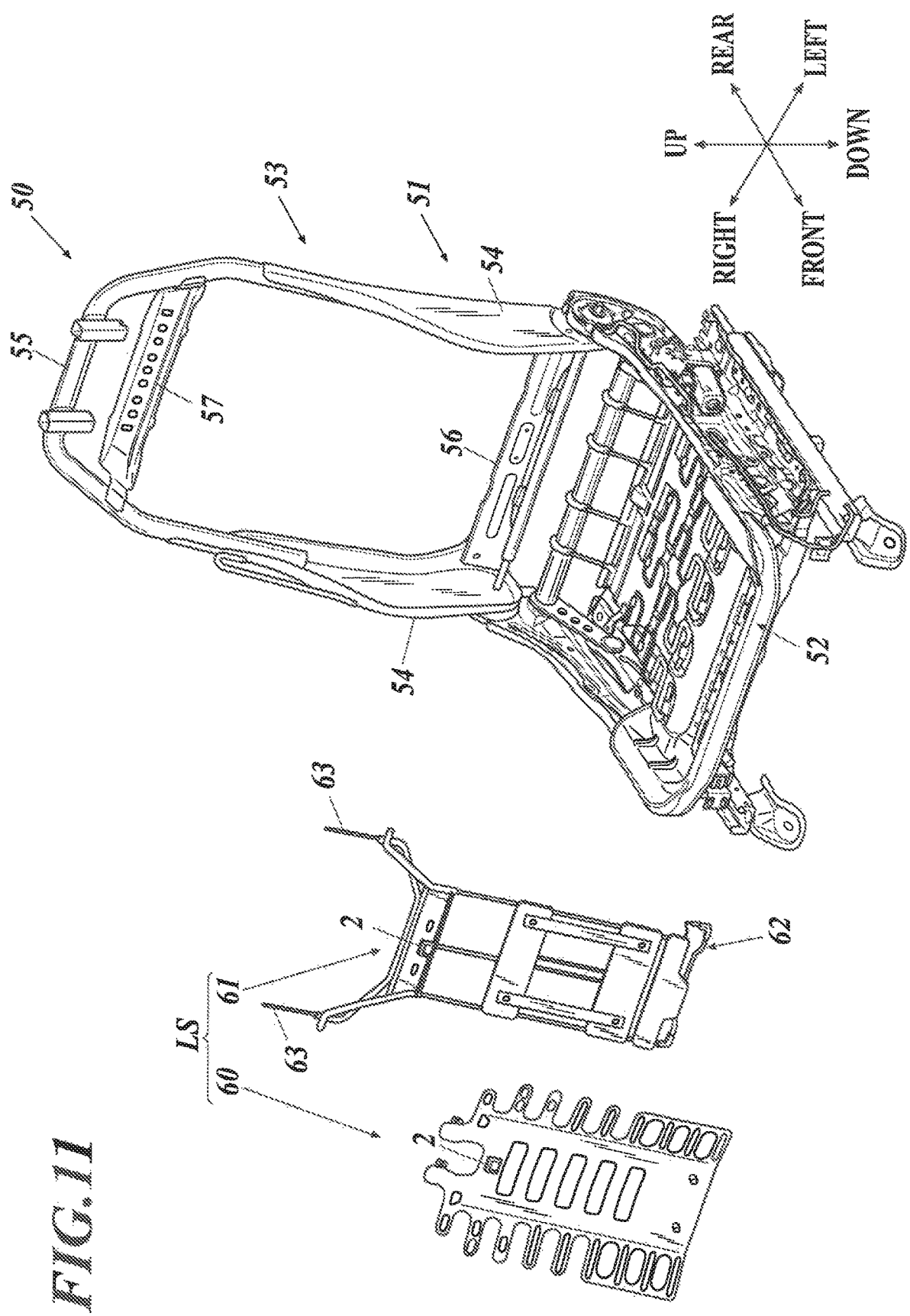
FIG. 11 is a perspective view showing a seat provided with a lumbar support device according to Modification 2.

The seat 50 in this modification includes a built-in seat frame 51 as shown in FIG. 11. The seat frame 51 includes a cushion frame 52 constituting a seat cushion and a seat back frame 43 constituting a seat back.

The cushion frame 52 and the seat back frame 53 are each provided with a cushion pad and further covered with a covering to constitute the seat 50.

The seat back frame 53 supports a lumbar support device LS which is a pressure receiving member. The seat back frame 53 includes a pair of metal plate frames 54 and a pipe frame 55. The paired metal plate frames 54 are arranged separately in the left-right direction. The pipe frame 55 is connected to the upper edges of the respective paired metal plate frames 54 and formed of a pipe material bending into a U-shape.

The seat back frame 53 includes a lower frame 56 and a bridging frame 57. The lower frame 56 functions as a connecting member which connects the lower portions of the metal plate frames 54 and as a support part. The bridging frame 57 functions as a bridging member which connects the left and right of the pipe frame 55.

The lower frame 56 is a member composed of a metal plate whose upper edge and the lower edge extend slightly forward in a cross-sectional view. The left and right edges of the lower frame 56 are welded to be fixed to the portions extending inside in the left-right direction of the metal plate frames 54.

The lumbar support device LS is attached to the seat back frame 53, receives pressure from the occupant leaning against the seat back and sends it to the seat back frame 53, and changes the shape of portions contacting the lumbar region of the occupant. As a result, supporting condition of the lumbar region can be changed according to the preference of the occupant.

The lumbar support device LS includes a pressure receiving plate 60, a support member 61, a lower latching portion 62, and a wire(s) 63. The pressure receiving plate 60 is made of resin and receives load from the back of the occupant through a cushion member (not shown). The support member 61 supports the pressure receiving plate 60 and changes the shape of the pressure receiving plate 60. The lower latch 62 fixes the lower portion of the support member 61 (lumbar support device LS) to the lower frame 56. The wire(s) 63 fix the upper edge of the support member 61 to the bridging frame 57.

The biological sensor 2 is provided in the lumbar support device LS. In the present modification, metal parts constituting the support member 61 is the member interfering with the passage of electromagnetic waves, and the biological sensor 2 is arranged at a position avoiding the metal parts constituting the support member 61.

More specifically, the biological sensor 2 is provided on the surface of the resin pressure receiving plate 60 or at a portion other than the metal parts constituting the support member 61, corresponding to the position of the human heart.

According to the present embodiment as described above, the biological sensor 2 is arranged in the seat 50 at a position avoiding the member 61 interfering with the passage of electromagnetic waves among the members constituting the seat 50. Therefore, the member 61 interfering with the passage of electromagnetic waves is less likely to interfere with the emission of electromagnetic waves from the biological sensor 2. This makes it easy to accurately detect biological information.

Furthermore, because the biological sensor 2 provided in the lumbar support device LS on the side of the seat back frame 53 is arranged corresponding to the human heart position, blood flow conditions can be grasped from the thoracic aorta. In such a case, biological information can be detected more easily than the case from thin blood vessels with less blood flow.

[Modification 3]

Figure 12:
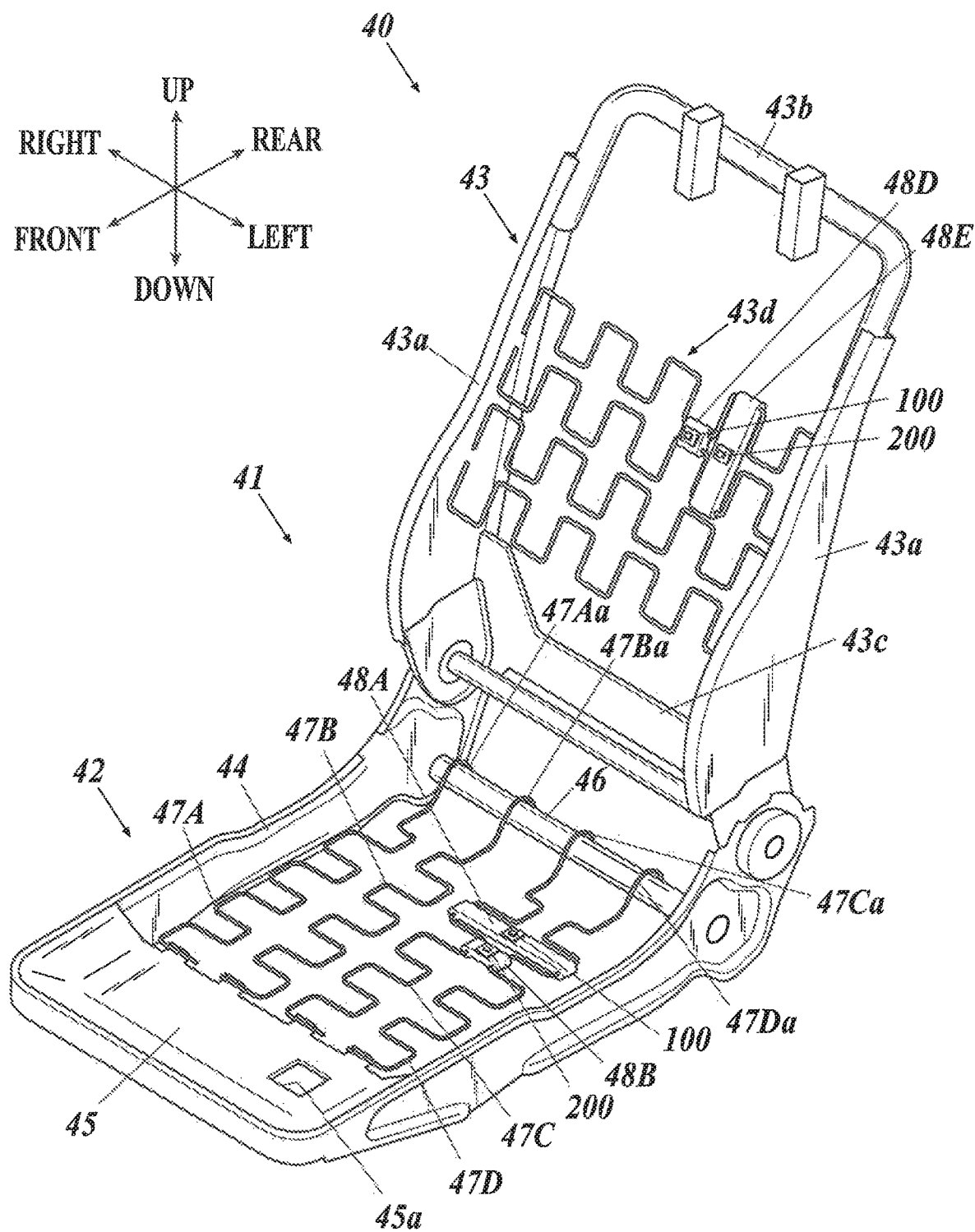
FIG. 12 is a perspective view showing a seat in which spring members are built in a seat cushion according to Modification 3.

The seat 40 in this modification includes a built-in seat frame 41 as shown in FIG. 12. The seat frame 41 includes a cushion frame 42 constituting a seat cushion and a seat back frame 43 constituting a seat back.

The cushion frame 42 and the seat back frame 43 are each provided with a cushion pad 42a and further covered with a covering 42b to constitute the seat 40.

The cushion frame 42 has a frame shape in a plan view and includes a pair of side frames 44, a pan frame 45, and a connecting pipe 46. The paired side frames 44 each extend long in the front-rear direction and are spaced separately in the left-right direction. The pan frame 45 is composed of a metal plate connecting the front edges of the paired side frames 44. The connection pipe 46 is formed of a metal pipe which connects the rear edges of the paired side frames 44.

A seat spring 47 is installed between the pan frame 45 and the connecting pipe 46.

First, the cushion frame 42 will be explained.

The seat spring 47 in the cushion frame 42 includes four spring members 47A to 47D which extend long in the front-rear direction and are arranged in the left-right direction.

Each of the spring members 47A to 47D is a bending metal wire. The rear ends of the spring members 47A to 47D are respectively formed into hooks 47Aa to 47Da to be hooked to the connecting pipe 46. The spring members 47A to 47D respectively extend forward from the hooks 47Aa to 47Da, each bending to the left and right directions to form zigzags. As shown in FIG. 12, the spring members 47A to 47D have respective front edges each connected to the pan frame 45 so as not to be displaced.

The cushion frame 42 is provided with the first sensor 100 and the second sensor 200, which are biological sensors. In the present modification, the spring members 47A to 47D are the members interfering with the passage of electromagnetic waves, and the first sensor 100 and the second sensor 200 are arranged at positions avoiding the spring members 47A to 47D.

More specifically, the first sensor 100 and the second sensor 200 are provided, as shown in FIG. 12, on the resin connecting members 48A and 48B connecting the spring materials 47C and 47D. That is, the first sensor 100 is provided on the connecting member 48A, and the second sensor 200 is provided on the connecting member 48B.

The positions of the first sensor 100 and the second sensor 200 correspond to the middle portion of the left and right sciatic bones of human buttocks or correspond to the position of the thigh. When the biological sensor(s) are provided at the portion(s) corresponding to the position of the thigh, the portion(s) may correspond to either one thigh or both thighs.

The first sensor 100 and the second sensor 200 are arranged at positions closer to the human than the connecting members 48A to 48D and the spring members 47A to 47D are. Since the first sensor 100 and the second sensor 200 are provided on such connecting members 48A to 48D, the measurement by the first sensor 100 and the second sensor 200 is less affected by the spring members 47A to 47D.

In FIG. 12, the connecting member 48A connects distant portions in the zigzag portions of the adjacent spring members 47C and 47D (47A and 47B). The first sensor 100 and the second sensor 200 provided on the connection member 48A can be arranged so as to overlap the spring members 47C or 47D (47A or 47B).

In FIG. 12, the connecting member 48B connects nearby portions in the zigzag portions of the adjacent spring members 47C and 47D (47A and 47B). The first sensor 100 and the second sensor 200 provided on the connection member 48B may be arranged so as to overlap the spring members 47C or 47D (47A or 47B).

Figure 13:
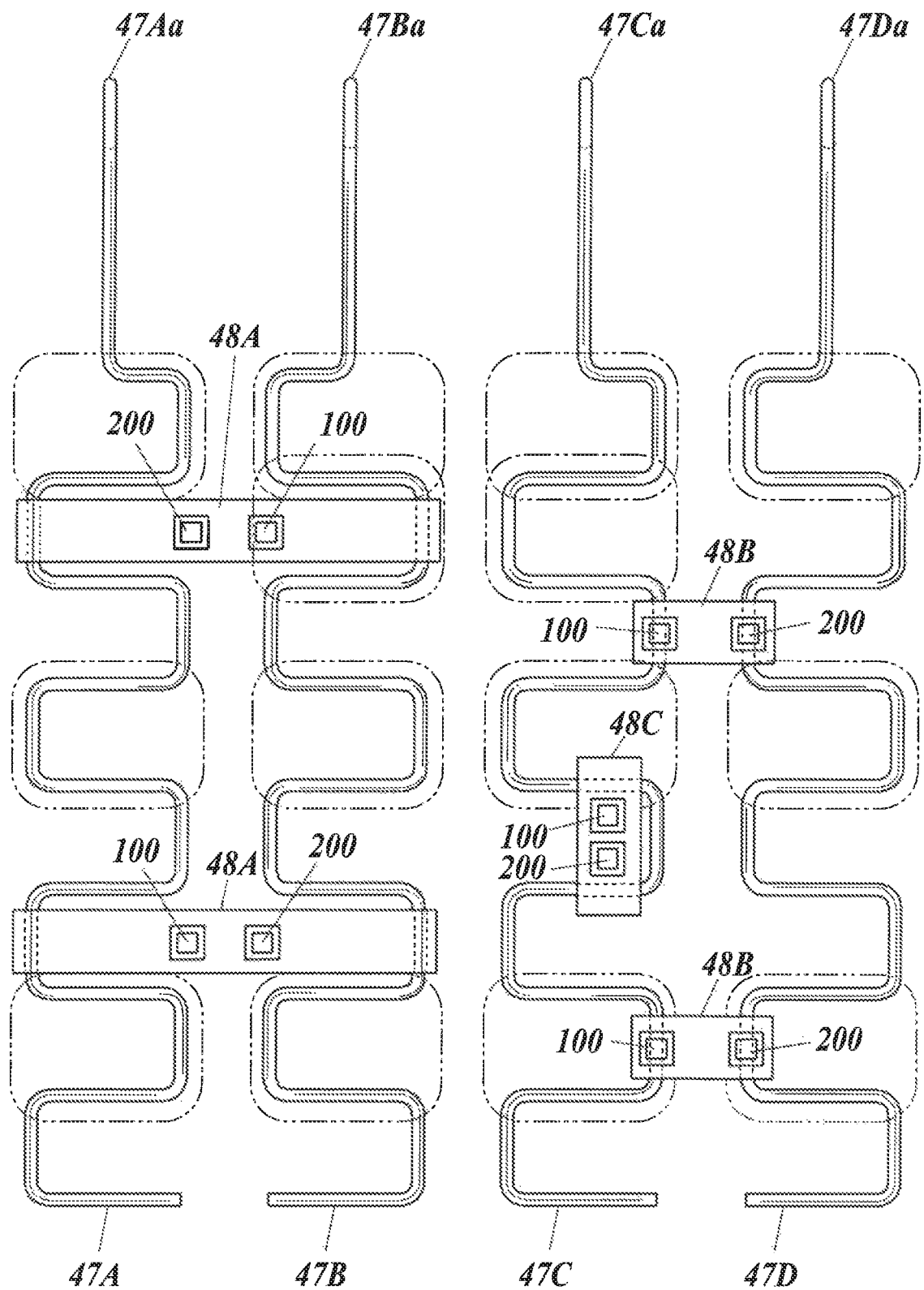
FIG. 13 is a plan view showing spring members according to Modification 3.

In the example shown in FIG. 12, the above connecting members 48A and 48B are provided so as to connect the adjacent spring members 47C and 47D. However, as shown in FIG. 13, the connecting members 48A and 48B may be provided so as to appropriately connect the respective spring members 47A to 47D. As well as another connecting member 48C in FIG. 13, the zigzag portions of each of the spring members 47A to 47D each bending to form zigzags may be connected to each other. The first sensor 100 and the second sensor 200 can be also arranged on such connecting member 48C.

In other words, the above-described connecting members 48A to 48C are installation plates each having a plate-shaped portion on whose upper surface the first sensor 100 or the second sensor 200 is installed. That is, the first sensor 100 and the second sensor 200 are arranged on the connecting members 48A to 48C in the present modification as described above, but are not limited thereto. The installation plates to be used may be a plate-like member located under the cushion pad 42a and having an upper surface on which the first sensor 100 and the second sensor 200 are installed (that is, installation plates having forms different from those as the connecting members 48A to 48C).

As the first sensor 100 and the second sensor 200 may be disposed on each of the connecting members 48A to 48C, the cushion pad 42a of the seat 40 has a recess 420 which can accommodate the first sensor 100 and the second sensor 200. The recess 420 is formed at a portion located above the portion where the first sensor 100 and the second sensor 200 is installed. As shown in FIG. 14, the recess 420 is formed by recessing the lower surface of the cushion pad 42a.

Furthermore, because the spring members 47A to 47D have respective front edges each connected to the pan frame 45 so as not to be displaced as described above, the first sensor 100 and the second sensor 200 installed at the respective connecting members 48A to 48D can also be prevented from being displaced.

Furthermore, the first sensor 100 and the second sensor 200 may also be arranged on the pan frame 45. Since the pan frame 45 is a member made of metal plate as described above and interferes with the passage of electromagnetic waves, the first sensor 100 and the second sensor 200 are preferably arranged on the upper side of the pan frame 45. That is, the first sensor 100 and the second sensor 200 are arranged at positions closer to the human than a member (pan frame 45) interfering with the passage of electromagnetic waves is.

When arranged on the upper surface of the pan frame 45, the first sensor 100 and the second sensor 200 may be arranged either at a flat portion near the center or at an inclined portion near the periphery of the pan frame 45.

However, the first sensor 100 and the second sensor 200 may be arranged at positions farther from the human than the pan frame 4 is arranged, if they are arranged at portions corresponding to an opening 45a formed in the pan frame 45 as shown in FIG. 12. By arranging the first sensor 100 and the second sensor 200 in this way, electromagnetic waves can be emitted toward the human through the opening 45a.

Furthermore, instead of the pan frame 45, the front edges of the paired side frames 44 may be connected to each other using a frame material or a pipe material (not shown). In this case, the front edges of the respective spring members 47A to 47D may be connected to the frame material or pipe material. The first sensor 100 and the second sensor 200 may be arranged with a clip or the like (not shown) on the frame material or the pipe material provided instead of the pan frame 45 as described above.

Furthermore, as shown in FIG. 14, the first sensor 100 and the second sensor 200 may be provided so as to be embedded in the cushion pad 42a of the cushion frame 42. If the first sensor 100 and the second sensor 200 are provided so as to be embedded in the cushion pad 42a, the cushion pad 42a itself may be formed by so-called insert molding where the first sensor 100 and the second sensor 200 are formed in an embedded state. If the first sensor 100 and the second sensor 200 are provided so as to be embedded in the cushion pad 42a, a recess (not shown) for accommodating the first sensor 100 and the second sensor 200 may be formed in the cushion pad 42a so that the first sensor 100 and the second sensor 200 can be easily installed.

The method for providing the first sensor 100 and the second sensor 200 embedded in the cushion pad 42a is not limited to the insert molding described above. The first sensor 100 and the second sensor 200 are preferably embedded even after the cushion pad 42a has been molded. That is, a part of the cushion pad 42a (detachable portion 422 in FIG. 14) may be formed to be detachable, and a recess 421 for accommodating the first sensor 100 and the second sensor 200 may be formed at a position corresponding to the detachable portion 422.

If the first sensor 100 and the second sensor 200 are provided so as to be embedded in the cushion pad 42a, the detachable portion 422 is detached, the first sensor 100 and the second sensor 200 are accommodated in the recess 421, and the detachable portion 422 is returned to be fitted again. In this way, the first sensor 100 and the second sensor 200 can be embedded in the cushion pad 42a.

In the present modification, the detachable portion 422 can be detached from the lower surface side of the cushion pad 42a, but may be detached from the upper surface side.

There may be formed a space in the cushion pad 42a for wiring a harness (not shown) not only for embedding the first sensor 100 and the second sensor 200, but for electrically connecting the first sensor 100 and the second sensor 200 and an external device (for example, a power generation element, a storage, a control device, and the like).

Furthermore, as shown in FIG. 14, a seating sensor 3 may be provided in the cushion pad 42a to detect that the human is seated on the seat 10. The biological sensor 100, 200 is linked to the seating sensor 3, and are set to operate when the seating sensor 3 detects that the human is seated on the seat 10.

As shown in FIG. 13, the first sensor 100 and the second sensor 200 may be arranged in reverse order. That is, while each of the two connecting members 48A connecting the spring members 47A and 47B is provided with the first sensor 100 and the second sensor 200 as shown in FIG. 13, the first sensor 100 and the second sensor 200 provided on one connecting member 48A and the first sensor 100 and the second sensor 200 provided on the other connecting member 48A are arranged in reverse order. Even in such a case, biological information can be detected.

Next, the seat back frame 43 will be explained.

As shown in FIG. 12, the seat back frame 43 is provided with a pair of side frames 43a, an upper frame 43b, and a lower member 43c. The paired side frames 43a each extend long in the up-down direction and are spaced separately in the left-right direction. The upper frame 43b is provided between the upper edges of the paired side frames 43a. The lower member 43c is a plate like member provided between the lower edges of the paired side frames 43a. A seat spring 43d composed of multiple spring members is provided so as to link the paired side frames 43a between the upper frame 43d and the lower member 43c.

The multiple spring members of the seat spring 43d each extend in the left-right direction and bend up and down to form zigzags.

The first sensor 100 and the second sensor 200 can be also provided on the above-described seat back frame 43, as well as on the above-described cushion frame 42.

That is, the first sensor 100 and the second sensor 200 may be provided on either one or both of the paired side frames 43a. In that case, the first sensor 100 and the second sensor 200 may be attached to either the inner surface or the outer surface of the side frames 43a.

The first sensor 100 and the second sensor 200 may be provided on the front surface of the lower member 43c. When the first sensor 100 and the second sensor 200 are arranged on the rear surface side of the metal lower member 43c, the first sensor 100 and the second sensor 200 are arranged so as to correspond to the position of an opening (not shown) formed in the lower member 43c.

Furthermore, the first sensor 100 and the second sensor 200 may be provided on the seat spring 43d. In that case, as shown in FIG. 12, the first sensor 100 is provided on the connection member 48D configured similarly to the connection member 48B and connecting the spring members. The second sensor 200 is provided on the connection member 48E configured similarly to the connection member 48A and connecting the spring members. If the spring members is not uniform in density, the first sensor 100 and the second sensor 200 may be arranged at portions where the density of the spring members is low.

The first sensor 100 and the second sensor 200 may be embedded in a cushion pad (not shown) provided on the front surface side of the seat back frame 43, in the same way as the side of the above-described cushion frame 42.

According to the present embodiment, one of the first sensor 100 and the second sensor 200 may be used for detection of biological information including noise, and the other is used for detection of noise. Therefore, only the biological information can be extracted by subtraction of the noise. Furthermore, because the first sensor 100 and the second sensor 200 are arranged adjacent to each other, there is little detection error between the first sensor 100 and the second sensor 200. Accordingly, it is easy to accurately detect biological information.

Furthermore, according to the present modification, the first sensor 100 and the second sensor 200 are arranged in the seat 40 at positions avoiding the member(s) 47A to 47D interfering with the passage of electromagnetic waves among the members constituting the seat 40. Therefore, the member(s) 47A to 47D interfering with the passage of electromagnetic waves are less likely to interfere with the emission of electromagnetic waves from the first sensor 100 and the second sensor 200. This makes it easy to accurately detect biological information.

Furthermore, because the first sensor 100 and the second sensor 200 provided in the cushion frame 42 are arranged at portions corresponding to the middle portion of the left and right sciatic bones of the human buttocks, the first sensor 100 and the second sensor 200 can be arranged so as not to knock the sciatic bones, such that the comfort when the human is seated on the seat is not impaired. Furthermore, because the first sensor 100 and the second sensor 200 provided in the cushion frame 42 is arranged at a portion corresponding to the position of the thighs, the blood flow condition of the popliteal arteries can be grasped. In such a case, biological information can be detected more easily than in the case of thin blood vessels with less blood flow.

Furthermore, the resin installation plate (connecting members 48A to 48E) attached to the member(s) 47A to 47D and 43d interfering with the passage of electromagnetic waves are arranged at respective positions closer to the human than the member(s) 47A to 47D and 43d are. The first sensor 100 and the second sensor 200 are arranged on the installation plates. Therefore, even if the first sensor 100 and the second sensor 200 are arranged in the vicinity of the member(s) 47A to 47D and 43d interfering with the passage of the electromagnetic waves, the first sensor 100 and the second sensor 200 are not easily affected by the member (s) 47A to 47D and 43d interfering with the passage of the electromagnetic waves.

Furthermore, in the seat 40, the first sensor 100 and the second sensor 200 are arranged at positions corresponding to the position of an opening 45a and being farther from the human than the member (pan frame 45, lower member 43c) interfering with the passage of electromagnetic waves is. The opening 45a is formed in the member 45, 43c interfering with the passage of electromagnetic waves. Therefore, even if the first sensor 100 and the second sensor 200 are arranged at positions farther from the human than the member 45, 43*c* interfering with the passage of electromagnetic waves are arranged in the seat 40, the first sensor 100 and the second sensor 200 are not easily affected by the member 45, 43*c* interfering with the passage of electromagnetic waves.

In addition, the member(s) 47A to 47D and 43*d* interfering with the passage of electromagnetic waves are arranged inside the seat 40 so as not to be uniform in density, and the first sensor 100 and the second sensor 200 are arranged at portions where the density of the member(s) 47A to 47B interfering with the passage of electromagnetic waves is low. Therefore, compared with the case where the first sensor 100 and the second sensor 200 are arranged at portions where the density of the member(s) 47A to 47B interfering with the passage of electromagnetic waves is high, the first sensor 100 and the second sensor 200 are not easily affected by the member(s) 47A to 47D and 43*d* interfering with the passage of electromagnetic waves.

Furthermore, the cushion pad 42*a* in the seat 40 has a part (detachable portion 422) which is configured to be detachable, and includes a recess 421 which accommodates the first sensor 100 and the second sensor 200 at positions corresponding to the portion 422. Therefore, a space for arranging the first sensor 100 and the second sensor 200 can be secured in the seat 40.

Furthermore, because the cushion pad 42*a* in the seat 40 is formed with the first sensor 100 and the second sensor 200 embedded therein, installation of the seat 40 can be efficiently performed with the first sensor 100 and the second sensor 200 embedded in the cushion pad 42*a*.

[Modification 4]

Figure 15:
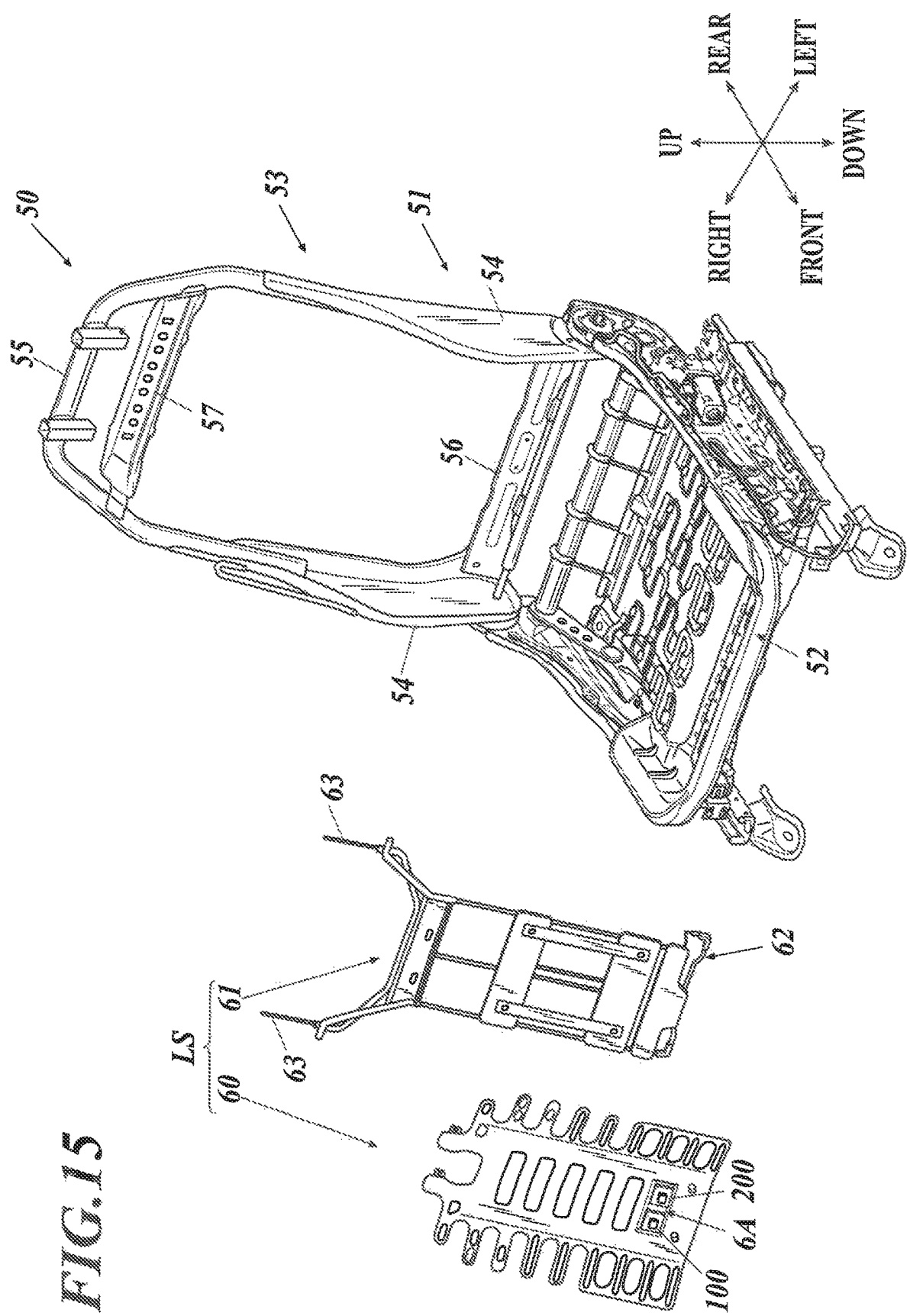
FIG. 15 is a perspective view showing a seat provided with a lumbar support device according to Modification 4.

The seat 50 in this modification includes a built-in seat frame 51 as shown in FIG. 15. The seat frame 51 includes a cushion frame 52 constituting a seat cushion and a seat back frame 43 constituting a seat back.

The cushion frame 52 and the seat back frame 53 are each provided with a cushion pad and further covered with a covering to constitute the seat 50.

The seat back frame 53 supports a lumbar support device LS which is a pressure receiving member. The seat back frame 53 includes a pair of metal plate frames 54 and a pipe frame 55. The paired metal plate frames 54 are arranged separately in the left-right direction. The pipe frame 55 is connected to the upper edges of the respective paired metal plate frames 54 and formed of a pipe material bending into a U-shape.

The seat back frame 53 includes a lower frame 56 and a bridging frame 57. The lower frame 56 functions as a connecting member which connects the lower portions of the metal plate frames 54 and as a support part. The bridging frame 57 functions as a bridging member which connects the left and right of the pipe frame 55.

The lower frame 56 is a member composed of a metal plate whose upper edge and the lower edge extend slightly forward in a cross-sectional view. The left and right edges of the lower frame 56 are welded to be fixed to the portions extending inside in the left-right direction of the metal plate frames 54.

The lumbar support device LS is attached to the seat back frame 53, receives pressure from the occupant leaning against the seat back and sends it to the seat back frame 53, and changes the shape of portions contacting the lumbar region of the occupant. As a result, supporting condition of the lumbar region can be changed according to the preference of the occupant.

The lumbar support device LS includes a pressure receiving plate 60, a support member 61, a lower latching portion 62, and a wire(s) 63. The pressure receiving plate 60 is made of resin and receives load from the back of the occupant through a cushion member (not shown). The support member 61 supports the pressure receiving plate 60 and changes the shape of the pressure receiving plate 60. The lower latch 62 fixes the lower portion of the support member 61 (lumbar support device LS) to the lower frame 56. The wire(s) 63 fix the upper edge of the support member 61 to the bridging frame 57.

The first sensor 100 and the second sensor 200 are provided in the lumbar support device LS. In the present modification, metal parts constituting the support member 61 is the member interfering with the passage of electromagnetic waves, and the first sensor 100 and the second sensor 200 are arranged at positions avoiding the metal parts constituting the support member 61.

More specifically, a mounting portion 64 for mounting the first sensor 100 and the second sensor 200 is integrally formed in the resin pressure receiving plate 60 of the lumbar support device LS. In other words, the first sensor 100 and the second sensor 200 form a unit including the pressure receiving plate 60 in the lumbar support device LS.

The mounting portion 64 includes a first recess where the first sensor 100 can be fitted to be mounted, and a second recess where the second sensor 200 can be fitted to be mounted. In use, the first sensor 100 is fitted and mounted to the first recess, and the second sensor 200 is fitted and mounted to the second recess.

The mounting positions of the first sensor 100 and the second sensor 200 may be reversed if the first sensor 100 and the second sensor 200 have the same shape, and the first recess and the second recess are also formed in the same shape.

According to the present modification, the first sensor 100 and the second sensor 200 in the seat 50 are arranged at positions avoiding the member 61 interfering with the passage of electromagnetic waves among the members constituting the seat 50. Therefore, the member 61 interfering with the passage of electromagnetic waves is less likely to interfere with the emission of electromagnetic waves from the first sensor 100 and the second sensor 200. This makes it easy to accurately detect biological information.

Furthermore, since the biological sensor 100, 200 forms a unit such that the first sensor 100 and the second sensor 200 are arranged adjacent to each other, the first sensor 100 and the second sensor 200 can be easily handled to be attached to the seat 50.

[Modification 5]

Figure 16:
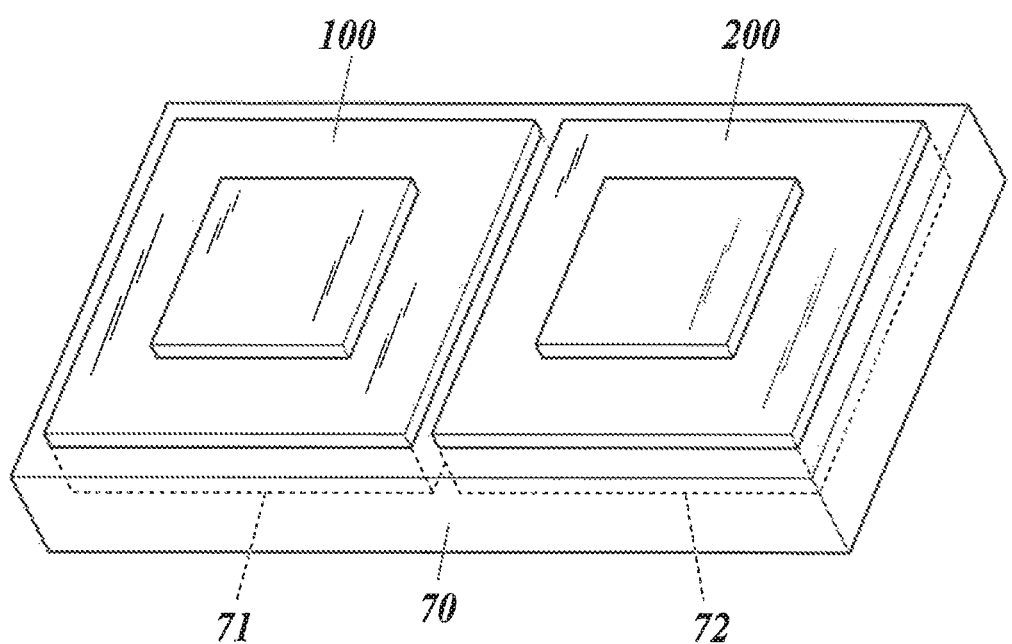
FIG. 16 is a perspective view showing the biological sensors according to Modification 5 forming a unit.

The biological sensor 100, 200 in this modification forms a unit such that the first sensor 100 and the second sensor 200 are arranged adjacent to each other as shown in FIG. 16.

That is, in the present modification, a housing 70 where the first sensor 100 and the second sensor 200 are mounted is used. The housing 70 includes a first recess 71 where the first sensor 100 can be fitted to be mounted, and a second recess 72 where the second sensor 200 can be fitted to be mounted.

In use, the first sensor 100 is fitted and mounted to the first recess 71, and the second sensor 200 is fitted and mounted to the second recess 72.

The mounting positions of the first sensor 100 and the second sensor 200 may be reversed if the first sensor 100 and the second sensor 200 have the same shape, and the first recess 71 and the second recess 72 are also formed in the same shape.

When the first sensor 100 and the second sensor 200 forming a unit with the housing 70 are arranged on the seat, the housing 70 itself is attached to an appropriate position of the seat, so that the first sensor 100 and the second sensor 200 can be arranged.

According to the present modification, since the biological sensor 100, 200 is a unit with the housing 70 where the first sensor 100 and the second sensor 200 are arranged adjacent to each other, the first sensor 100 and the second sensor 200 can be easily handled to be attached to the seat 50.

[Modification 6]

In the above-described embodiment, the biological sensor is integrated with a receiver that receives electromagnetic waves emitted from each of the first sensor 100 and the second sensor 200. However, in the present modification, the biological sensor 100, 200 has a receiver 3 as a separate piece.

The receiver 3 as a separate piece is provided along with the first sensor 100 and the second sensor 200 as shown in FIGS. 17A to 17D. There may be provided one receiver 3 which receives the reflected electromagnetic waves emitted by the first sensor 100 and the second sensor 200, or multiple receivers 3 each corresponding to the first sensor 100 or the second sensor 200.

Furthermore, in the above-described embodiment, the first sensor 100 and the second sensor 200 are arranged so as to be parallel or substantially parallel to the surface to be seated of the seat 10. However, in the present modification, the first sensor 100 and the second sensor 200 may be arranged inclined (at some angle) with respect to the surface to be seated of the seat 80. That is, the first sensor 100 and the second sensor 200 may be arranged in parallel or substantially parallel to the surface to be seated of the seat 80, or non-parallel to the surface to be seated of the seat 80.

The seat 80 of the present modification includes a seat cushion 81 and a seat back 84.

In FIGS. 17A to 17D, the first sensor 100 and the second sensor 200 are arranged adjacent to each other in the left-right direction. The receivers 3 are provided below the first sensor 100 and the second sensor 200. The arrangement directions of the receivers 3 with respect to the first sensor 100 and the second sensor 200 are not particularly limited. The receivers 3 are provided on the lower side of the first sensor 100 and the second sensor 200 in the example shown in FIGS. 17A to 17D, but may be provided on the upper side or may be provided on the lateral side.

In FIGS. 17A to 17D, the bidirectional arrow Y represents the spread (surface direction) of the surface to be seated in a lateral view of the seat 80.

As well as the first sensor 100 and the second sensor 200, the receiver 3 may be arranged in parallel or substantially parallel to the surface to be seated of the seat 80, or non-parallel to the surface to be seated of the seat 80.

Figure 17A:
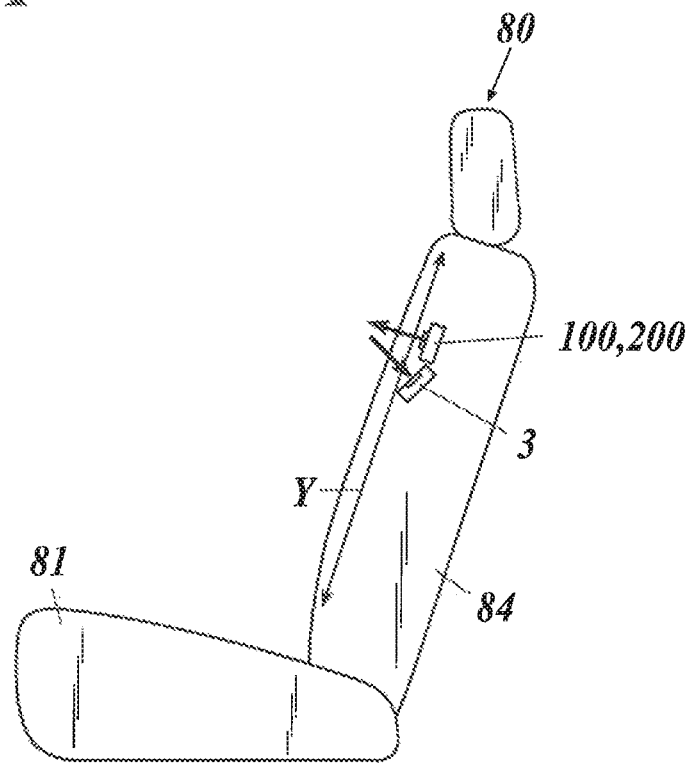
FIG. 17A is a diagram illustrating an arrangement example of a first sensor, a second sensor, and a receiver according to Modification 6.

In the example shown in FIG. 17A, the first sensor 100 and the second sensor 200 are each arranged so as to be parallel to the surface to be seated of the seat 80, and the receiver 3 is arranged so as to be non-parallel to the surface to be seated of the seat 80.

Figure 17B:
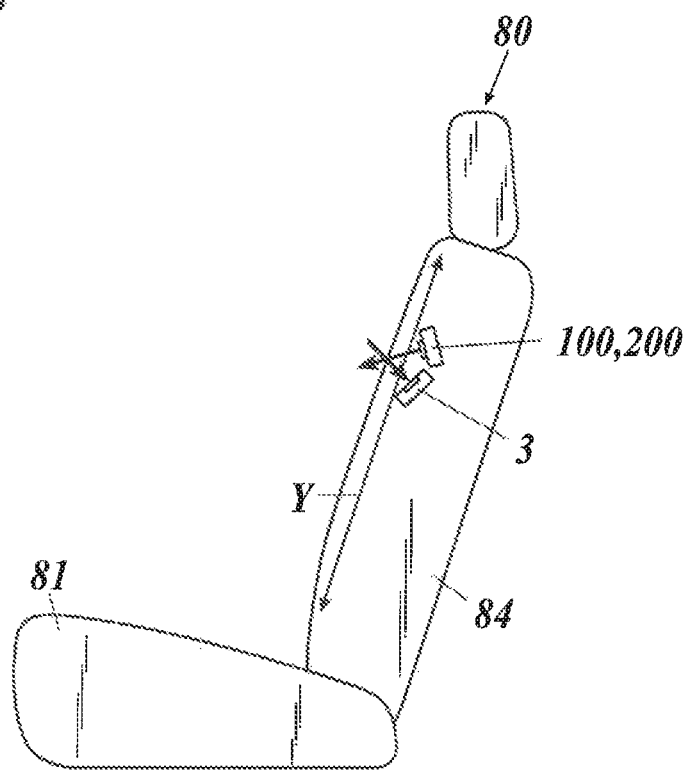
FIG. 17B is a diagram illustrating an arrangement example of a first sensor, a second sensor, and a receiver according to Modification 6.

In the example shown in FIG. 17B, the first sensor 100 and the second sensor 200 are each arranged so as to be non-parallel to the surface to be seated of the seat 80, and the receiver 3 is arranged so as to be non-parallel to the surface to be seated of the seat 80, such that the electromagnetic wave emission direction from the first sensor 100 and the second sensor 200 each intersect the electromagnetic wave receiving direction by the receiver 3.

Figure 17C:
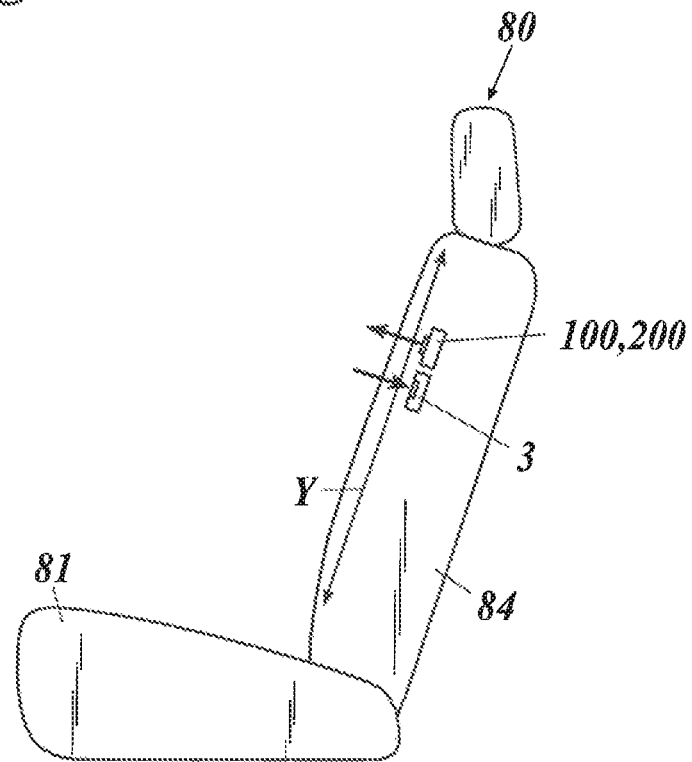
FIG. 17C is a diagram illustrating an arrangement example of a first sensor, a second sensor, and a receiver according to Modification 6.

In the example shown in FIG. 17C, the first sensor 100 and the second sensor 200 are each arranged so as to be parallel to the surface to be seated of the seat 80, and the receiver 3 is also arranged so as to be parallel to the surface to be seated of the seat 80.

Figure 17D:
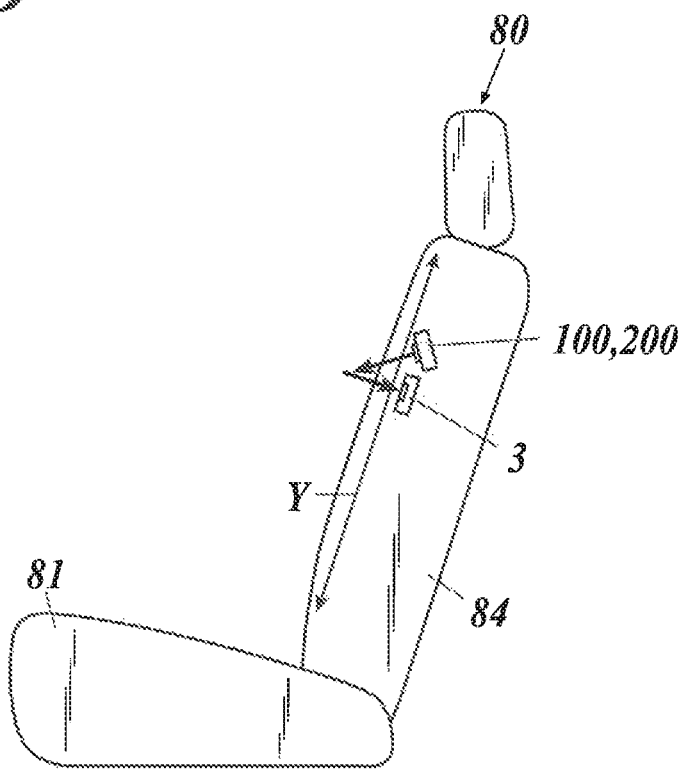
FIG. 17D is a diagram illustrating an arrangement example of a first sensor, a second sensor, and a receiver according to Modification 6.

In the example shown in FIG. 17D, the first sensor 100 and the second sensor 200 are each arranged so as to be non-parallel to the surface to be seated of the seat 80, and the receiver 3 is arranged so as to be parallel to the surface to be seated of the seat 80.

The arrangement structures in FIGS. 17A to 17D can also be applied to the case where the receiver 3 is provided on the lateral side of the first sensor 100 and the second sensor 200.

The arrangement structures of the first sensor 100, the second sensor 200, and the receiver 3 in the present modification can also be applied to the seat cushion.

According to the present modification, because the receivers 3 which receive the electromagnetic waves emitted from the first sensor 100 and the second sensor 200 are provided side by side with respect to the first sensor 100 and the second sensor 200, there is little detection error between the first sensor 100 and the second sensor 200. Therefore, it is easy to accurately detect biological information.

Furthermore, the receiving accuracy of the electromagnetic waves by the receiver 3 can be adjusted by appropriately changing the angles of the first sensor 100, the second sensor 200, and the receiving unit 3 with respect to the surface to be seated of the seat 80. Therefore, it is easy to more accurately detect biological information.

[Modification 7]

In the above-described embodiment, the biological sensors 100, 200 are arranged at at least two respective portions of the seat 10 which are separate from each other, that is, at least two portions in the seat cushion 11 and in the seat back 14.

That is, the seat cushion 11 may be provided with one or more couples of the first sensor 100 and the second sensor 200, and the seat back 14 may be provided with one or more couples of the first sensor 100 and the second sensor 200. Alternatively, two or more couples of the first sensor 100 and the second sensor 200 may be provided only in the seat cushion 11. Alternatively, two or more couples of the first sensor 100 and the second sensor 200 may be provided only in the seat back 14.

Figure 18:
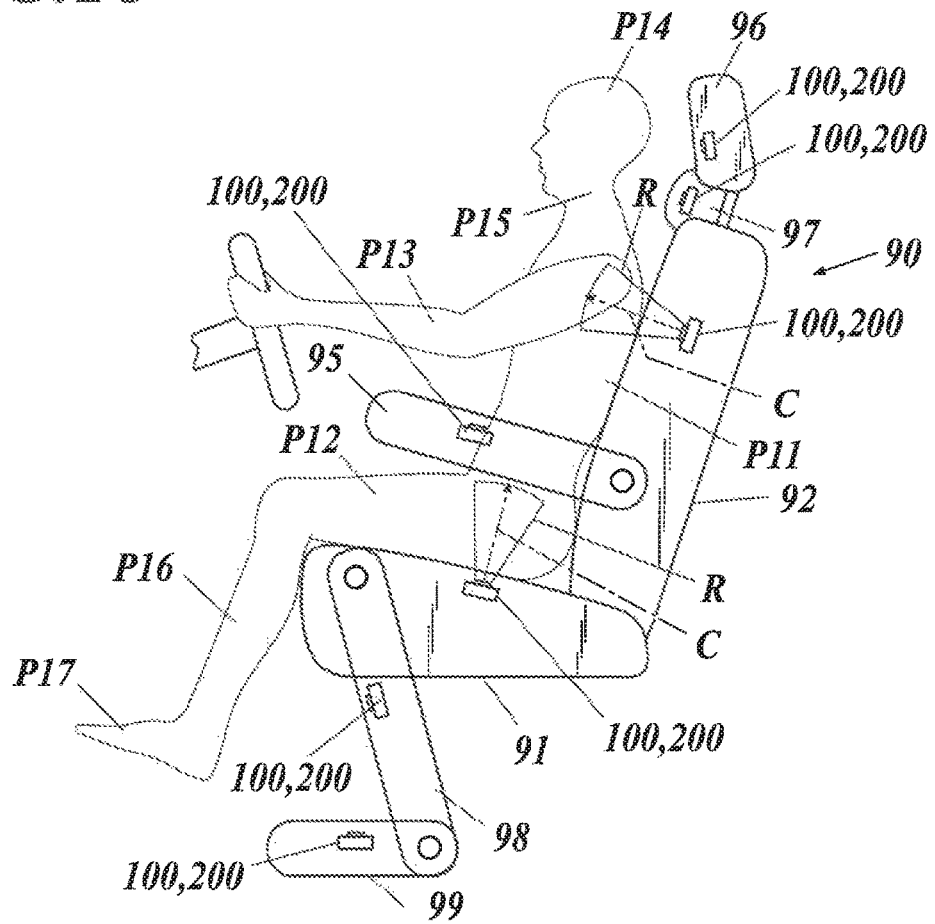
FIG. 18 is a diagram illustrating an arrangement example of biological sensors in the seat provided with movable portions according to Modification 7.
Figure 19:
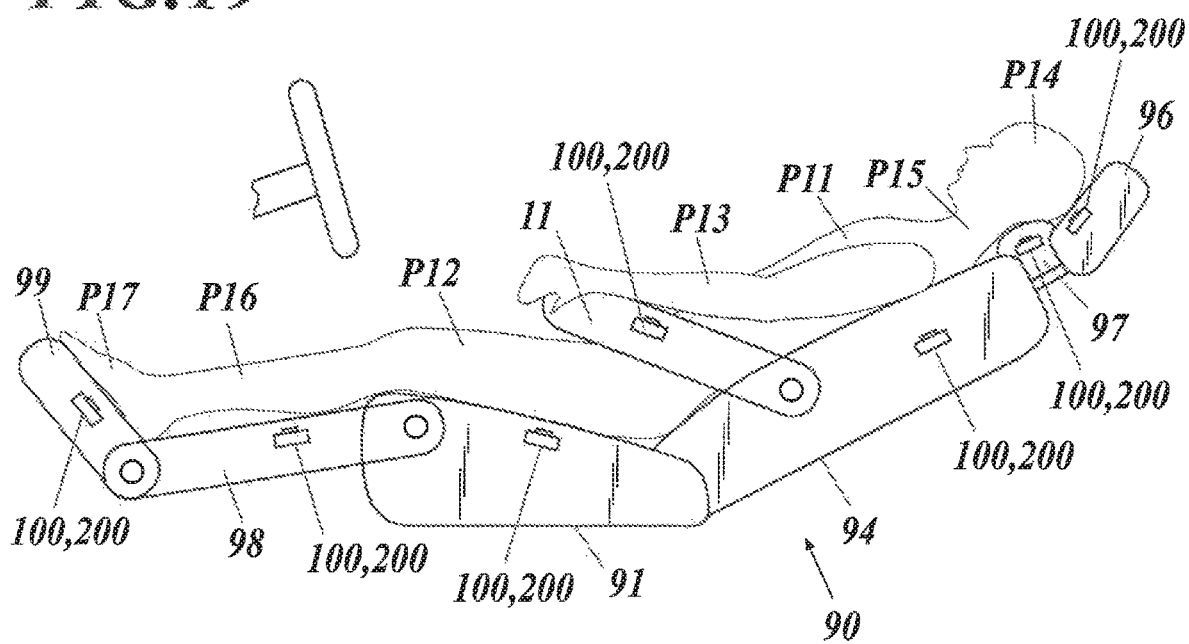
FIG. 19 is a diagram illustrating a positional relationship between an occupant and biological sensors when a seat provided with movable portions according to Modified 7 is in a reclined state.

As shown in FIGS. 18 and 19, in the present modification, the seat 90 includes a seat cushion 91, a seat back 94, and movable portions 95 to 99. The seat cushion 91 supports human buttocks and thighs. The seat back 94 has a lower edge supported by the seat cushion 11. The movable portions 95 to 99 are connected to either of the seat cushion 91 or the seat back 94 and move with respect to either the seat cushion 91 or the seat back 94.

The biological sensor 100, 200 is provided at at least one of the seat cushion 91, the seat back 94, and the movable parts 95 to 99.

The seat cushion 91 supports the thighs P12 of the human seated on the seat 90, and the seat back 94 supports the trunk P11. The trunk P11 includes shoulders, a chest, an abdomen, a lumbar region, and buttocks. The buttocks may be supported by the seat cushion 91. The seat cushion 91 and the seat back 94 compose the seat body of the seat 90, and the movable portions 95 to 99 are connected to the seat body.

The movable portions 95 to 99 include an armrest 95 which supports an arm P13 of the human seated on the seat 90, a headrest 12 which supports the head P14, a neckrest 13 which supports the neck P15 of the occupant P, an ottoman 14 which supports the leg P16, and a footrest 15 which supports the foot P17.

In the present modification, the biological sensor 100, 200 is provided in each of the seat cushion 91, the seat back 94, and the movable portions 95 to 99. In the present modification, the first sensors 100 are arranged next to the respective the second sensors 200 in the left-right direction of the seat 90.

In the example shown in FIG. 18, the biological information can be detected by the biological sensors 100, 200 while the seat 90 is not reclined. In this case, the biological information is detected by the first sensor 100 and the second sensor 200 provided in each of the seat cushion 91 and the seat back 94.

In the example shown in FIG. 19, the biological information can be detected by the biological sensors 100, 200 while the seat 90 is reclined. In this case, the biological information is detected by the biological sensors 100, 200 provided in the entire seat 90. Alternatively, the biological information may be detected by the biological sensors 100, 200 provided at each of two or more portions selected as appropriate.

In the present modification, since the biological sensor 100, 200 is provided at at least one of the seat cushion 91, the seat back 94, and the movable parts 95 to 99, the biological information can be detected from various parts of the human body. As a result, it is possible to improve accuracy in measurement of the human health condition by detection of biological information.

Furthermore, because the movable portions 95 to 99 are configured to be movable with respect to the seat cushion 91 and the seat back 94, the biological information can be detected when the seat 90 is either reclined or not. As a result, the seat 90 can be suitably mounted and applied to a vehicle capable of traveling through either one of autonomous driving and manual driving which can be switched to each other, for example.

INDUSTRIAL APPLICABILITY

The arrangement structure of the biological sensor according to the present invention has high industrial applicability because the member interfering with the passage of electromagnetic waves is less likely to interfere with electromagnetic waves emitted from biological sensor so that biological information can be detected easily and accurately.

REFERENCE SIGNS LIST

A1 Member Interfering with Passage of Electromagnetic Waves
A2 Member Interfering with Passage of Electromagnetic Waves
A3 Member Interfering with Passage of Electromagnetic Waves
R Emission Range
C Emission Center
1 Biological Sensor
2 Biological Sensor
10 Seat
11 Seat Cushion
12 Cushion Pad
12a Groove
13 Covering
14 Seat Back
15 Cushion Pad
15a Groove
16 Covering
17 Headrest
20 Seat Heater
21 Base Material
22 Heater Wire
22a Front Heater Wire
22b Central Heater Wire
22c Rear Heater Wire
23 Groove Heater Wire
30 Seat Heater
31 Base Material
32 Heater Wire
32a Upper Heater Wire
32b Central Heater Wire
32c Lower Heater Wire
33 Groove Heater Wire
100 First Sensor
200 Second Sensor

The invention claimed is:

1. An arrangement structure for a biological sensor comprising:
a biological sensor of a non-contact type provided in a seat on which a human is seated, the biological sensor being configured to emit electromagnetic waves and to detect biological information of the human with the electromagnetic waves; and
a receiver configured to receive reflected waves of the electromagnetic waves, wherein
the biological sensor is arranged non-parallel to a surface of the seat, on which the human is seated, at a position in the seat avoiding a member that constitutes the seat and interferes with passage of the electromagnetic waves, and
the receiver is arranged non-parallel to the surface.

2. The arrangement structure for a biological sensor according to claim 1,
wherein the seat is provided in a vehicle that travels through autonomous driving or manual driving that are able to be switched to each other.

3. The arrangement structure for a biological sensor according to claim 1,
wherein the biological sensor is arranged such that an emission center of the electromagnetic waves does not pass through the member.

4. The arrangement structure for a biological sensor according to claim 1,
wherein the biological sensor is arranged such that an emission range of the electromagnetic waves does not include the member.

5. The arrangement structure for a biological sensor according to claim 1,
wherein the biological sensor is arranged in the seat to be closer than the member to the human.

6. The arrangement structure for a biological sensor according to claim 5, further comprising:
a resin installation plate that is attached to the member and that is arranged at a position closer than the member to the human, wherein
the biological sensor is arranged on the installation plate.

7. The arrangement structure for a biological sensor according to claim 1, wherein
the member has an opening, and
the position of the biological sensor is farther than the member from the human, and the position of the biological sensor corresponds to a position of the opening.

8. The arrangement structure for a biological sensor according to claim 1, wherein
the member is arranged so as not to be uniform in density inside the seat, and
the biological sensor is arranged at a portion where density of the member is low.

9. The arrangement structure for a biological sensor according to claim 1, wherein
the seat includes a cushion pad that is covered by a covering, and
when a detachable portion of the cushion pad is detached, a space that accommodates the biological sensor is formed inside the cushion pad.

10. The arrangement structure for a biological sensor according to claim 1, wherein
the seat includes a cushion pad that is covered by a covering, and
the biological sensor is embedded in the cushion pad.

11. The arrangement structure for a biological sensor according to claim 1,
wherein the biological sensor includes two or more biological sensors that are arranged at at least two respective portions of the seat that are separate from each other.

12. The arrangement structure for a biological sensor according to claim 1, wherein
the biological sensor includes a first sensor and a second sensor that emit electromagnetic waves of different frequencies toward the human, and
the first sensor and the second sensor are arranged adjacent to each other.

13. The arrangement structure for a biological sensor according to claim 12,
wherein the biological sensor includes two or more biological sensors, including the first sensor and the second sensor, that are arranged at at least two respective portions of the seat that are separate from each other.

14. The arrangement structure for a biological sensor according to claim 12, wherein
the seat includes a seat cushion and a seat back, the seat cushion supporting a human buttock and a human thigh, and the seat back having a lower edge that is supported by the seat cushion,
the biological sensor is provided in at least one of the seat cushion and the seat back, and
the first sensor and the second sensor are arranged adjacent to each other in a surface direction of the surface.

15. The arrangement structure for a biological sensor according to claim 12, wherein
the seat includes a seat cushion and a seat back, the seat cushion supporting a human buttock and a human thigh, and the seat back having a lower edge supported by the seat cushion,
the biological sensor is provided in at least one of the seat cushion and the seat back, and
the first sensor and the second sensor are arranged adjacent to each other in a thickness direction of either the seat cushion or the seat back.

16. The arrangement structure for a biological sensor according to claim 1, wherein
the biological sensor is arranged at a different angle than the receiver with respect to the surface.

* * * * *